United States Patent [19]
Greenlee et al.

[11] Patent Number: 5,164,407
[45] Date of Patent: Nov. 17, 1992

[54] SUBSTITUTED IMIDAZO-FUSED 5-MEMBERED RING HETEROCYCLES AND THEIR USE AS ANGIOTENSIN II ANTAGONSISTS

[75] Inventors: William J. Greenlee, Teaneck; David B. R. Johnston, Warren; Malcolm MacCoss, Freehold; Nathan B. Mantlo, Westfield; Arthur A. Patchett, Westfield; Prasun K. Chakravarty, Edison; Thomas F. Walsh, Westfield, all of N.J.

[73] Assignee: Merck & Co., Inc., Rahway, N.J.

[21] Appl. No.: 516,502

[22] Filed: Apr. 25, 1990

Related U.S. Application Data

[63] Continuation-in-part of Ser. No. 375,655, Jul. 3, 1989, abandoned.

[51] Int. Cl.$^5$ .................... C07D 495/04; A61K 31/38
[52] U.S. Cl. ..................................... 514/381; 514/412; 514/414; 548/252; 548/253; 548/303.4; 548/303.1; 548/303.7
[58] Field of Search ....................... 548/253, 363, 252; 514/381, 412; 515/414

[56] References Cited

U.S. PATENT DOCUMENTS 4,880,804 11/1989 Carini et al. .................... 514/234.5

FOREIGN PATENT DOCUMENTS 245637 11/1987 European Pat. Off. .
399731 11/1990 European Pat. Off. .

OTHER PUBLICATIONS

Chiu et al., Eur. J. Pharm. Exp. Ther. 157, 13-21 (1988).
Wong et al., J. Pharm. Exp. Ther. 247, 1-7 (1988).

*Primary Examiner*—David B. Springer
*Attorney, Agent, or Firm*—William H. Nicholson; Joseph F. DiPrima

[57] ABSTRACT

There are disclosed new substituted imidazo-fused 5-membered ring heterocyclic compounds and derivatives thereof which are useful as angiotensin II antagonists. These compounds have the general formula:

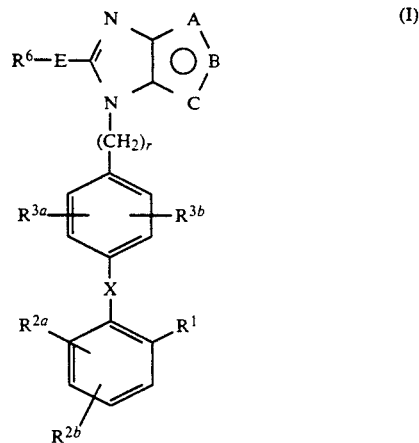

4 Claims, No Drawings

SUBSTITUTED IMIDAZO-FUSED 5-MEMBERED RING HETEROCYCLES AND THEIR USE AS ANGIOTENSIN II ANTAGONSISTS

INTRODUCTION OF THE INVENTION

This is a continuation-in-part of copending application Ser. No. 375,655 filed Jul. 3, 1989, abandoned.

This invention relates to novel substituted imidazo-fused-5-membered ring heterocyclic compounds and dervatives thereof which are useful as angiotensin II antagonists in the treatment of hypertension or congestive heart failure. Thus, the substituted imidazo-fused 5-membered ring heterocyclic compounds of the invention are useful as antihypertensives.

This invention also relates to novel processes for preparing the novel compounds of the invention; pharmaceutical formulations comprising one or more of the novel compounds as active ingredient(s); and, to a method of treating hypertension or congestive heart failure by administration of a novel compound of the invention to a patient in need of such treatment.

BACKGROUND OF THE INVENTION

Renin-angiotensin system (RAS) plays a central role in the regulation of normal blood pressure and seems to be critically involved in hypertension development and maintenance as well as in congestive heart failure. Angiotensin II (A II), an octapeptide hormone is produced mainly in the blood during the cleavage of angiotensin I by angiotensin converting enzyme (ACE) localized on the endothelium of blood vessels of lung, kidney, and many other organs, and as the end product of the RAS, A II is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. Clin. Exp. Hypertens. A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847 and 4,880,804; in European Patent Applications 028,834; 245,637; 253,310; and 291,969; and in articles by A. T. Chiu, et al. [Eur. J. Pharm. Exp. Therap, 157, 13–21 (1988)] and by P. C. Wong, et al. [*J. Pharm. Exp. Therap*, 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]pyridinge-6-carboxylic acid and analogs thereof as antihypertensive agents.

None of the compounds disclosed in the above identified U.S. Patents, European Applications and articles are the substituted imidazo-fused 5-membered ring heterocyclic compounds of this invention.

DETAILED DESCRIPTION OF THE INVENTION

This invention relates to novel substituted imidazo-fused 5-membered ring heterocyclic compounds and derivatives thereof which are useful as angiotensin II antagonists, as antihypertensives, in the treatment of congestive heart failure and in the treatment of elevated intraocular pressure. The compounds of this invention have the general formula:

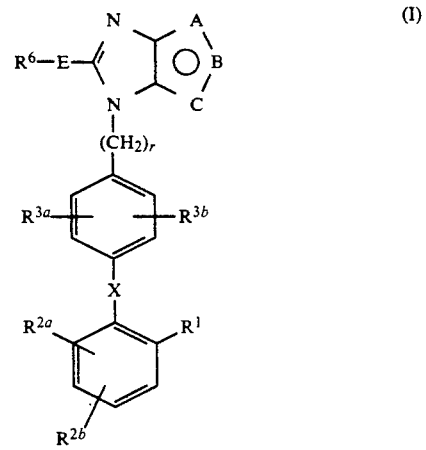

wherein:
$R^1$ is
(a) —$CO_2R^4$,
(b) —$SO_3R^5$,
(c) —$NHSO_2CF_3$,
(d) —$PO(OR^5)_2$,
(e) —$SO_2$—NH—$R^9$,

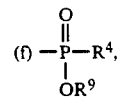

(g) —$SO_2NH$-heteroaryl as defined below,
(h) —$CH_2SO_2NH$-heteroaryl as defined below,
(i) —$SO_2NH$—CO—$R^{21}$
(j) —$CH_2SO_2NH$—CO—$R^{21}$,
(k) —CONH—$SO_2R^{21}$,
(l) —$CH_2CONH$—$SO_2R^{21}$,
(m) —$NHSO_2NHCO$—$R^{21}$,
(n) —$NHCONHSO_2R^{21}$,
(o) —$SO_2NHCONHR^{21}$,
(p) —CONHOR$^5$,

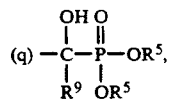

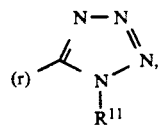

-continued (s) 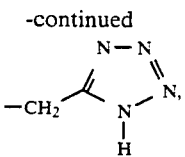 —CH$_2$ (t) 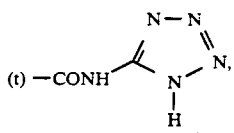 —CONH (u) —CONHNHSO$_2$CF$_3$,
(v) —SO$_2$NHCN, (w) 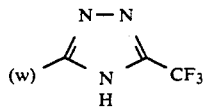

(x) 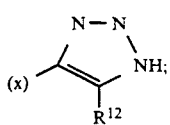

wherein:
heteroaryl is an unsubstituted, monosubstituted or disubstituted five or six membered aromatic ring which can optionally contain from 1 to 3 heteroatoms selected from the group consisting of O, N or S and wherein the substituents are members selected from the group consisting of —OH, —SH, —C$_1$-C$_4$-alkyl, —C$_4$-C$_4$-alkoxy, —CF$_3$, halo (Cl, Br, F, I), —NO$_2$, —CO$_2$H, —CO$_2$—C$_1$-C$_4$-alkyl, —NH$_2$, NH(C$_1$-C$_4$-alkyl) and —N(C$_1$-C$_4$-alkyl)$_2$;
R$^{2a}$ and R$^{2b}$ are independently H, halo (Cl, Br, I, F), —NO$_2$, —NH$_2$, C$_1$-C$_4$-alkylamino, di(C$_1$-C$_4$-alkyl)-amino, —SO$_2$NHR$^9$, CF$_3$, C$_1$-C$_4$-alkyl, or C$_1$-C$_4$-alkoxy;
R$^{3a}$ is
(a) H,
(b) halo(Cl, Br, I, F)
(c) C$_1$-C$_6$-alkyl,
(d) C$_1$-C$_6$-alkoxy,
(e) C$_1$-C$_6$-alkoxy-C$_1$-C$_4$-alkyl;
R$^{3b}$ is
(a) H,
(b) halo (Cl, Br, I, F)
(c) NO$_2$,
(d) C$_1$-C$_6$-alkyl,
(e) C$_1$-C$_6$-acyloxy,
(f) C$_3$-C$_7$-cycloalkyl
(g) C$_1$-C$_6$-alkoxy,
(h) —NHSO$_2$R$^4$,
(i) hydroxy C$_1$-C$_4$-alkyl,
(j) aryl C$_1$-C$_4$-alkyl
(k) C$_1$-C$_4$-alkylthio
(l) C$_1$-C$_4$-alkylsulfinyl
(m) C$_1$-C$_4$-alkylsulfonyl
(n) NH$_2$
(o) C$_1$-C$_4$-alkylamino
(p) di(C$_1$-C$_4$-alkyl)amino
(q) CF$_3$
(r) —SO$_2$—NHR$^9$
(s) aryl or,
(t) furyl;

wherein aryl is phenyl or naphthyl optionally substituted with one or two substituents selected from V and W as defined below;
R$^4$ is H, straight chain or branched C$_1$-C$_6$-alkyl, aryl, or aryl-C$_1$-C$_5$-alkyl wherein the aryl groups are as defined above and when a substituent, can be the same or different;
R$^{4a}$ is C$_1$-C$_6$-alkyl, aryl or aryl-C$_1$-C$_5$-alkyl;
R$^5$ is H or —CH(R$^4$)—O—CO—R$^{4a}$;
E is a single bond, —NR$^{13}$(CH$_2$)$_s$—, —S(O)$_x$(CH$_2$)$_s$— where X is 0 to 2 and s is 0 to 5, —CH(OH)—, —O—, —CO—;
R$^6$ is
(a) aryl as defined above;
(b) straight chain or branched C$_1$-C$_6$-alkyl, C$_3$-C$_7$-cycloalkyl, C$_2$-C$_5$-alkenyl or C$_2$-C$_5$-alkynyl each of which can be optionally substituted with a substituent selected from the group consisting of aryl as defined above, C$_3$-C$_7$-cycloalkyl, halo (Cl, Br, I, F) —OH, —NH$_2$, —NH(C$_1$-C$_4$-alkyl), —N(C$_1$-C$_4$-alkyl)$_2$, —NH—SO$_2$R$^4$, —COOR$^4$, —SO$_2$NHR$^9$; or
(c) an unsubstituted, monosubstituted or disubstituted hetero aromatic 5 or 6 membered ring which can contain one or two heteroatoms selected from the group consisting of N, O, S, and wherein the substituents are members selected from the group consisting of —OH, —SH, C$_1$-C$_4$-alkyl, C$_1$-C$_4$-alkyloxy, —CH$_3$, halo (Cl, Br, I, F), —CO$_2$R$^4$, or NO$_2$;
A—B—C together are:
(a) —N(R$^8$)—C(R$^{7a}$)=N—
(b) —N=C(R$^{7a}$)—N(R$^8$)—
(c) —C(R$^{7a}$)=N—N(R$^8$)—
(d) —N(R$^8$)—N=C(R$^{7a}$)—
(e) —Y—C(R$^{7a}$)=N—
(f) —N=C(R$^{7a}$)—Y—
(g) —C(R$^{7a}$)=N—Y—
(h) —Y—N=C(R$^{7a}$)—
(i) =N—Y—C(R$^{7a}$)=
(j) =C(R$^{7a}$)—Y—N=
(k) —C(R$^{7a}$)=C(R$^{7b}$)—N(R$^8$)—
(l) —C(R$^{7a}$)=C(R$^{7b}$)—Y—
(m) —N(R$^8$)—C(R$^{7a}$)=C(R$^{7b}$)—
(n) —Y—C(R$^{7a}$)=C(R$^{7b}$)—
(o) =C(R$^{7a}$)—N(R$^8$)—C(R$^{7b}$)=
(p) =C(R$^{7a}$)—Y—C(R$^{7b}$)=
(q) =N—Y—N=
(r) —N=N—N(R$^8$)—
(s) —N(R$^8$)—N=N—
(t) =N—N(R$^8$)—N=
(u) =N—N(R$^8$)—C(R$^{7a}$)=
(v) =C(R$^{7a}$)—N(R$^8$)—N=
(w) —C(R$^{7c}$)(R$^{7d}$)—O—C(=O)—
(x) —C(R$^{7c}$)(R$^{7d}$)—C(=O)—O—
(y) —O—C(=O)—C(R$^{7c}$)(R$^{7d}$)—
(z) —C(=O)—O—C(R$^{7c}$)(R$^{7d}$)—
(aa) —C(=O)—N(R$^8$)—C(R$^{7c}$)(R$^{7d}$)—
(bb) —C(R$^{7c}$)(R$^{7d}$)—N(R$^8$)—C(=O)—
Y is O, S, SO or SO$_2$
R$^{7a}$ and R$^{7b}$ are independently
(a) H,
(b) straight chain or branched C$_1$-C$_6$-alkyl, C$_2$-C$_6$-alkenyl or C$_2$-C$_6$-alkynyl each of which can be optionally substituted with a substituent selected from the group consisting of C$_3$-C$_7$ cycloalkyl, halo (Cl, Br, I, F), —OH, —NH$_2$, —NH(C$_1$-C$_4$ alkyl), —N(C$_1$–C$_4$ alkyl)$_2$, —NHSO$_2$R$^4$, —COOR$^4$, C$_1$–C$_4$-alkoxyl, C$_1$–C$_4$-alkylthio, C$_1$–C$_4$-alkylcarbonyl, —CONH$_2$, —OCOR$^4$, —CON(R$^4$)$_2$, aryl,

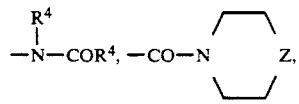

—S(O)$_x$—R$^{21}$, tetrazol-5-yl, —CONHSO$_2$R$^{21}$, —SO$_2$NH-hetroaryl wherein the heteroaryl is as first defined above, —SO$_2$NHCO—R$^{21}$, heteroaryl as first defined above, —PO(OR$^4$)$_2$, —PO(OR$^4$)R$^9$, (c) aryl as defined above,
(d) substituted aryl in which the substituents are V or W, as defined below,
(e) aryl-C$_1$–C$_4$-alkyl in which the aryl group as defined above can be unsubstituted or substituted with V or W as defined below,
(f) halo,
(g) hydroxy,
(h) —N(R$^4$)R$^{21}$,
(i) C$_1$–C$_6$-alkoxy,
(j) perfluoro-C$_1$–C$_4$-alkyl,
(k) CO$_2$R$^4$,
(l) CON(R$^4$)$_2$,
(m) N(R$^4$)-CO-R$^4$,
(n) —S(O)$_x$—R$^{21}$,

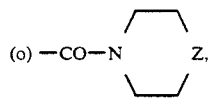

(p) tetrazol-5-yl,
(q) —CN,
(r) —CONHSO$_2$R$^{21}$,
(s) —SO$_2$NH-heteroaryl,
(t) —SO$_2$NHCOR$^{21}$,
(u) heteroaryl,
(v) —NHSO$_2$R$^{21}$,
(w) —NHSO$_2$CF$_3$,

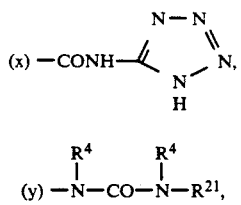

(z) —SO$_2$NH—CN, R$^4$
(aa) -N-CO$_2$R$^{21}$,
(bb) -PO(OR$^4$)$_2$,
(cc) -PO(OR$^4$)R$^9$,

R$^{7c}$ and R$^{7d}$ are independently
(a) H
(b) straight chain or branched C$_1$–C$_6$-alkyl, C$_2$–C$_6$-alkenyl or C$_2$–C$_6$-alkynyl each of which can be optionally substituted with a substituent selected from the group consisting of C$_3$–C$_7$-cycloalkyl, halo (Cl, Br, I, F), —OH, —NH$_2$, —NH(C$_1$–C$_4$-alkyl), —N(C$_1$–C$_4$ alkyl)$_2$, —NHSO$_2$R$^4$, —COOR$^4$, C$_1$–C$_4$-alkoxy, C$_1$–C$_4$-alkylthio, C$_1$–C$_4$-alkylcarbonyl, or —CONH$_2$,
(c) aryl as defined above,
(d) substituted aryl as defined above in which the substituents are V or W as defined below,
(e) aryl-C$_1$–C$_4$-alkyl in which the aryl group is as defined above and which can be unsubstituted or substituted with V or W as defined below.

R$^8$ is:
(a) H,
(b) straight chain or branched C$_1$–C$_6$-alkyl, C$_2$–C$_6$-alkenyl or C$_2$–C$_6$-alkynyl each of which can be optionally substituted with a substituent selected from the group consisting of C$_3$–C$_7$-cycloakyl, halo (Cl, Br, I, F), —OH, —NH$_2$, —NH(C$_1$–C$_4$-alkyl), —N(C$_1$–C$_4$ alkyl)$_2$, —NHSO$_2$R$^4$, —COOR$^4$, C$_1$–C$_4$-alkoxyl, C$_1$–C$_4$-alkylthio, —CONH$_2$, —COR$^4$, or —SO$_2$R$^4$,
(c) —COR$^4$
(d) aryl, or substituted aryl wherein the aryl groups are as defined above and the substituents are V or W as defined below,
(e) aryl-C$_1$–C$_4$-alkyl in which the aryl group is as defined above and can be unsubstituted, mono- or disubstituted with V or W as defined below;

V and W are independently:
(a) H,
(b) C$_1$–C$_5$-alkoxy,
(c) C$_1$–C$_5$-alkyl,
(d) hydroxy,
(e) C$_1$–C$_5$-alkyl-S(O)$_x$- where x is as defined above,
(f) CN,
(g) NO$_2$,
(h) NHR$^4$,
(i) N(R$^4$)$_2$,
(j) CON(R$^4$)$_2$,
(k) CO$_2$R$^4$,
(l) COR$^4$,
(m) CF$_3$,
(n) halo (Cl, Br, I, F),
(o) hydroxy-C$_1$–C$_5$-alkyl,
(p) C$_1$–C$_5$-alkylthio,
(q) —SO$_2$NR$^9$R$^{10}$,
(r) C$_3$–C$_7$-cycloalkyl,
(s) C$_2$–C$_{10}$-alkenyl, R$^9$ is H, C$_1$–C$_5$-alkyl, phenyl or benzyl;
R$^{10}$ is H, C$_1$–C$_4$-alkyl;
R$^{11}$ is H, C$_1$–C$_6$alkyl, C$_2$–C$_4$-alkenyl, C$_1$–C$_4$-alkoxy-C$_1$–C$_4$-alkyl, or -CH$_2$-C$_6$H$_4$R$^{20}$;
R$^{12}$ is —CN, —NO$_2$ or —CO$_2$R$^4$;
R$^{13}$ is H, C$_1$–C$_4$-acyl, C$_1$–C$_6$-alkyl, allyl, C$_3$–C$_6$-cycloalkyl, phenyl or benzyl;
R$^{14}$ is H, C$_1$–C$_8$-alkyl, C$_1$–C$_8$-perfluoroalkyl, C$_3$–C$_6$-cycloalkyl, phenyl or benzyl;
R$^{15}$ is H, C$_1$–C$_6$-alkyl;
R$^{16}$ is H, C$_1$–C$_6$-alkyl, C$_3$–C$_6$-cycloalkyl, phenyl or benzyl;
R$^{17}$ is —NR$^9$R$^{10}$, —OR$^{10}$, —NHCONH$_2$, —NHCSNH$_2$,

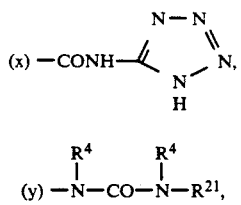

R$^{18}$ and R$^{19}$ are independently C$_1$–C$_4$-alkyl or taken together are —(CH$_2$)$_q$— where q is 2 or 3;

$R^{20}$ is H, —NO$_2$, —NH$_2$, —OH or —OCH$_3$;
$R^{21}$ is
  (a) aryl as defined above,
  (b) heteroaryl as defined above,
  (c) C$_3$-C$_7$-cycloalkyl,
  (d) C$_1$-C$_4$-alkyl optionally substituted with a substituents selected from the group consisting of aryl as defined above, heteroaryl as defined above, —OH, —SH, C$_1$-C$_4$-alkyl, —O(C$_1$-C$_4$-alkyl), —S(C$_1$-C$_4$-alkyl), —CF$_3$, halo (Cl, Br, F, I), —NO2, —CO$_2$H, CO$_2$-C$_1$-C$_4$-alkyl, —NH$_2$, —NH(C$_1$-C$_4$-alkyl), —N(C$_1$-C$_4$-alkyl)$_2$, —PO$_3$H, —PO(OH)(O—C$_1$-C$_4$-alkyl);
  (e) perfluoro-C$_1$-C$_4$-alkyl;
X is:
  (a) a single bond,
  (b) —CO—,
  (c) —O—,
  (d) —S—, (e) 

(f) 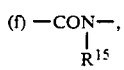

(g) 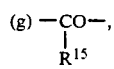

(h) —OCH$_2$—,
  (i) —CH$_2$O—
  (j) —SCH$_2$—,
  (k) —CH$_2$S—,
  (l) —NHC(R$^9$)(R$^{10}$)—,
  (m) —NR$^9$SO$_2$—,
  (n) —SO$_2$NR$^9$—,
  (o) —C(R$^9$)(R$^{10}$)NH—,
  (p) —CH=CH—,
  (q) —CF=CF—,
  (r) —CH=CF—,
  (s) —CF=CH—,
  (t) —CH$_2$CH$_2$—,
  (u) —CF$_2$CF$_2$—, (v) 

(w) 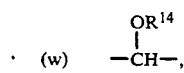

(x) 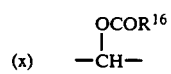

(y) 

(z) 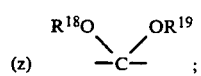 ;

Z is O, NR$^{13}$ or S;
r is 1 or 2; and,
the pharmaceutically acceptable salts thereof.

One embodiment of the compounds of Formula (I) are those wherein:

$R^1$ is (a) —COOH, (b) 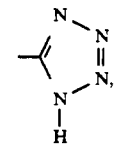

(c) —NHSO$_2$CF$_3$;
  (d) —SO$_2$NH-heteroaryl as defined below,
  (e) —CH$_2$SO$_2$NH-heteroaryl as defined below,
  (f) —SO$_2$NH—CO—R$^{21}$
  (g) —CH$_2$SO$_2$NH—CO—R$^{21}$,
  (h) —CONH—SO$_2$R$^{21}$,
  (i) —CH$_2$CONH—SO$_2$R$^{21}$,
  (j) —NHSO$_2$NHCO—R$^{21}$,
  (k) —NHCONHSO$_2$R$^{21}$,
$R^{2a}$ is H;
$R^{2b}$ is H, Cl, C$_1$-C$_4$-alkyl, or C$_1$-C$_4$-alkoxy;
$R^{3a}$ is H;
$R^{3b}$ is H, Cl, C$_1$-C$_4$-alkyl, C$_5$-C$_6$-cycloalkyl, or C$_1$-C$_4$-alkoxy;
$R^4$ is H or C$_1$-C$_4$-alkyl;
E is a single bond, or —S—;
$R^6$ is C$_1$-C$_5$-alkyl;
X is a single bond;
r is one;
A—B—C together are:
  (a) =C(R$^{7a}$)—Y—C(R$^{7b}$)=
  (b) =C(R$^{7a}$)—N(R$^8$)—C(R$^{7b}$)=
  (c) —N(R$^8$)—C(R$^{7a}$)=N—
  (d) —N=C(R$^{7a}$)—N(R$^8$)—
  (e) —N(R$^8$)—N=C(R$^{7a}$)
  (f) —C(R$^{7a}$)=N—N(R$^8$)—
  (g) —C(R$^{7a}$)=C(R$^{7b}$)—Y—
  (h) —Y—C(R$^{7a}$)=C(R$^{7b}$)—
  (i) —N=C(R$^{7a}$)—Y—
  (j) —Y—C(R$^{7a}$)=N—
  (k) —C(R$^{7a}$)=N—Y—
  (l) —Y—N=C(R$^{7a}$)—
  (m) —C(=O)—O—C(R$^{7c}$)(R$^{7d}$)—
  (n) —C(=O)—N(R$^8$)—C(R$^{7c}$)(R$^{7d}$)—
  (o) —C(R$^{7c}$)(R$^{7d}$)—O—C(=O)—
  (p) —C(R$^{7c}$)(R$^{7d}$)—N(R$^8$)—C(=O)—
  (q) =N—S—N=
  (r) =C(R$^{7a}$)—Y—N=
  (s) =N—Y—C(R$^{7a}$)=
Y is S, O, SO, or SO$_2$;
$R^{7a}$ and $R^{7b}$ are independently:
  (a) H;
  (b) straight chain or branched C$_1$-C$_6$-alkyl, C$_2$-C$_6$-alkenyl or C$_2$-C$_6$-alkynyl each of which can be optionally substituted with OH, CO$_2$R$^4$, NHR$^4$, N(R$^4$)$_2$ or CON(R$^4$)$_2$;
  (c) aryl or aryl-C$_1$-C$_4$-alkyl wherein the aryl can be optionally substituted with H, halo (Cl, Br, I, F), C$_1$-C$_4$-alkyl, hydroxy-C$_1$-C$_4$-alkyl, C$_1$-C$_4$-alkoxy or CO$_2$R$^4$;
  (d) C$_1$-C$_4$-alkoxy;
  (e) CO$_2$R$^4$;
  (f) CON(R$^4$)$_2$;
  (g) C$_1$-C$_4$-alkylthio;
  (h) halo (Cl, Br, F, I);
  (i) NH$_2$;
  (j) NH(C$_1$-C$_4$-alkyl);
  (k) N(C$_1$-C$_4$-alkyl)$_2$;
  (l) CF$_3$;

$R^{7c}$ and $R^{7d}$ are independently H, alkyl or substituted alkyl, aryl, substituted aryl or substituted aryl-$C_1$–$C_4$-alkyl, wherein substituents can be H, halo, $C_1$–$C_4$-alkyl, hydroxy-$C_1$–$C_4$-alkyl, $CO_2R^4$, or $COR^4$;

$R^8$ is:
 (a) H;
 (b) $C_1$–$C_6$-alkyl optionally substituted with OH, $CO_2R^4$, $N(R^4)_2$, or $CON(R^4)_2$;
 (c) aryl or aryl-$C_1$–$C_4$-alkyl wherein the aryl moiety is optionally substituted with H, halo, $C_1$–$C_4$-alkyl, hydroxy-$C_1$–$C_4$-alkyl, $CO_2R^4$; $COR^4$, or $SO_2R^4$.

One class of compounds representative of this embodiment are those wherein:

A—B—C together are $=C(R^{7a})$—Y—$C(R^{7b})=$;
Y is S, O, SO or $SO_2$;
$R^{7a}$ and $R^{7b}$ are independently:
 (a) H;
 (b) straight chain or branched $C_1$–$C_6$-alkyl, $C_2$–$C_6$-alkenyl or $C_2$–$C_6$-alkynyl each of which can be optionally substituted with OH, $CO_2R^4$, $NHR^4$, $N(R^4)_2$ or $CON(R^4)_2$;
 (c) aryl or aryl-$C_1$–$C_4$-alkyl wherein the aryl can be optionally substituted with H, halo (Cl, Br, I, F), hydroxy-$C_1$–$C_4$-alkyl, $C_1$–$C_4$-alkyl, $C_1$–$C_4$-alkoxy or $CO_2R^4$;
 (d) $C_1$–$C_4$-alkoxy;
 (e) $CO_2R^4$
 (f) $CON(R^4)_2$;
 (g) $C_1$–$C_4$-alkylthio;
 (h) $CF_3$;

Illustrative compounds within this class are:
(1) 4'-[(2-butyl-1H-thieno[3,4-d]imidazol-1-yl) methyl]-[1,1'-biphenyl]-2-carboxylic acid;
(2) 2-propyl-1-[(2'-{1H-tetrazol-5-yl}{1,1'-biphenyl}-4-yl)methyl-1H-furo[3,4-d]imidazole;
(3) 2-butyl-4-methyl-1-[2'-{1H-tetrazol-5-yl}{1,1'-biphenyl-4-yl)methyl]-1H-thieno[3,4-d]imidazole;
(4) 1-[(2'-carboxy{1,1'-biphenyl}-4-yl)methyl]-4-methyl-2-propyl-1H-thieno[3,4-d]imidazole 5-oxide; and,
(5) 4-ethyl-2-propyl-1-[(2'-{1H-tetrazol-5-yl}-{1,1'-biphenyl}-4-yl)methyl]-1H-thieno[3,4-d]imidazole 5,5-dioxide; and,
(6) 4-ethyl-2-propyl-1-[2'-{N-acetyl)sulfonamido}{1,1'-biphen}-4-yl)methyl]-1H-thieno-[3,4-d]-imidazole 5,5-dioxide.

Another class of compounds representing this embodiment are those wherein:

A—B—C together are $=C(R^{7a})$—$N(R^8)$—$C(R^{7b})=$;
$R^{7a}$ and $R^{7b}$ are independently:
 (a) H;
 (b) straight chain or branched $C_1$–$C_6$-alkyl, $C_2$–$C_6$-alkenyl or $C_2$–$C_6$-alkynyl each of which can be optionally substituted with OH, $CO_2R^4$, $NHR^4$, $N(R^4)_2$ or $CON(R^4)_2$;
 (c) aryl or aryl-$C_1$–$C_4$-alkyl wherein the aryl can be optionally substituted with H, halo (Cl, Br, I, F), $C_1$–$C_4$-alkyl, hydroxy-$C_1$–$C_4$-alkyl, $C_1$–$C_4$-alkoxy or $CO_2R^4$;
 (d) $C_1$–$C_4$-alkoxy;
 (e) $CO_2R^4$;
 (f) $CON(R^4)_2$;
 (g) $C_1$–$C_4$-alkylthio;
 (h) $CF_3$;

$R^8$ is:
 (a) H;
 (b) $C_1$–$C_6$-alkyl optionally substituted with OH, $CO_2R^4$, $N(R^4)_2$, or $CON(R^4)_2$;
 (c) aryl or aryl-$C_1$–$C_4$-alkyl wherein the aryl moiety is optionally substituted with H, halo, $C_1$–$C_4$-alkyl, hydroxy-$C_1$–$C_4$-alkyl, $CO_2R^4$; $COR^4$, or $SO_2R^4$.

Illustrative compounds within this class are:
(1) 4'-[(2-butyl-1,5-dihydro-5-methylpyrrolo[3,4-d]-imidazol-1-yl)methyl][1,1'-biphenyl]-2-carboxylic acid;
(2) 5-acetyl-1,5-dihydro-2-propyl-1-[(2'-{1H-tetrazol-5-yl}-{1,1'-biphenyl}-4-yl)methyl]pyrrolo[3,4-d]-imidazole;
(3) 2-butyl-1,5-dihydro-4,5-dimethyl-1-[(2'-{1H-tetrazol-5-yl}{1,1'-biphenyl}-4-yl)methyl]pyrrolo[3,4-d]-imidazole;
(4) 2-butyl-4-ethyl-1,5-dihydro-5-(methylsulfonyl)-1-[(2'-{1H-tetrazol-5-yl}{1, 1'-biphenyl}-4-yl)methyl]pyrrolo-[3,4-d]imidazole; and
(5) 2-butyl-1,5-dihydro-4,5-dimethyl-1-[2'-{(N-acetyl)sulfonamido}{1,1'-biphenyl}-4-yl) methyl]-pyrrolo[3,4-d]imidazole.

A futher class of compounds representing this embodiment are those wherein:

A—B—C together are
 (a) —$N(R^8)$—$C(R^{7a})=N$—;
 (b) —$N=C(R^{7a})$—$N(R^8)$—;
 (c) —$N(R^8)$—$N=C(R^{7a})$—;
 (d) —$C(R^{7a})=N$—$N(R^8)$—;

$R^{7a}$ is:
 (a) H;
 (b) straight chain or branched $C_1$–$C_6$-alkyl, $C_2$–$C_6$-alkenyl or $C_2$–$C_6$-alkynyl each of which can be optionally substituted with OH, $CO_2R^4$, $NHR^4$, $N(R^4)_2$ or $CON(R^4)_2$;
 (c) aryl or aryl-$C_1$–$C_4$-alkyl wherein the aryl can be optionally substituted with H, halo (Cl, Br, I, F), $C_1$–$C_4$-alkyl, hydroxy-$C_1$–$C_4$-alkyl, $C_1$–$C_4$-alkoxy or $CO_2R^4$;
 (d) $NH_2$;
 (e) $NH(C_1$–$C_4$-alkyl);
 (f) $N(C_1$–$C_4$-alkyl)$_2$;
 (g) $C_1$–$C_6$-alkoxy;
 (h) $CF_3$;

$R^8$ is:
 (a) H;
 (b) $C_1$–$C_6$-alkyl optionally substituted with OH, $CO_2R^4$, $N(R^4)_2$, or $CON(R^4)_2$;
 (c) aryl or aryl-$C_1$–$C_4$-alkyl where the aryl is optionally substituted with H, halo, $C_1$–$C_4$-alkyl, hydroxy-$C_1$–$C_4$-alkyl, $CO_2R^4$; $COR^4$, or $SO_2R^4$.

Illustrative compounds within this class are:
(1) 4'-[(2-butyl-1,4-dihydro-4-methylimidazo[4,5-d]-imidazol-1-yl)methyl][1,1'-biphenyl]-2-carboxylic acid;
(2) 1,4-dihydro-1-methyl-5-propyl-4-[(2'-{1H-tetrazol-5-yl}{1,1'-biphenyl}-4-yl) methyl]imidazo[4,5-d]-imidazole-2-methanol;
(3) 5-butyl-1-ethyl-1,4-dihydro-2-methyl-4-[(2'-{1H-tetrazol-5-yl}{1,1'-biphenyl}-4-yl) methyl]imidazo[4,5-d]-imidazole;
(4) 4'-[(2-butyl-1,6-dihydro-6-methylimidazo[4,5-d]-imidazol-1-yl)methyl][1,1'-biphenyl]-2-carboxylic acid;
(5) 1,6-dihydro-1-methyl-2-propyl-6-[(2'-{1H-tetrazol-5-yl}{1,1'-biphenyl}-4-yl)methyl]imidazo[4,5-d]-imidazole-2-methanol;

(6) 1,4-dihydro-1,3-dimethyl-5-propyl-4-[(2'-{1H-tetrazol-5-yl}{1,1'-biphenyl}-4-yl)methyl-]imidazo[4,5-c]pyrazole;

(7) 1,6-dihydro-1,3-dimethyl-5-propyl-6-[(2'-{1H-tetrazol-5-yl}{1,1'-biphenyl}-4-yl)methyl-}imidazo[4,5-c]-pyrazole;

(8) 1,4-dihydro-1,2-dimethyl-5-propyl-4-[(2'-{1H-tetrazol-5-yl}{1,1'-biphenyl}-4-yl) methyl-]imidazo[4,5-d]-imidazole;

(9) 1,6-dihydro-1,2-dimethyl-5-propyl-6-[(2'-{1H-tetrazol-5-yl}{1,1'-biphenyl}-4-yl) methyl-]imidazo[4,5-d]-imidazole;

(10) 4'-[(1,4-dihydro-1,2-dimethyl-5-propylimidazo[4,5-d]-imidazol-4-yl)methyl][1,1'-biphenyl]-2-carboxylic acid;

(11) 4'[(1,6-dihydro-1,2-dimethyl-5-propylimidazo[4,5-d]-imidazol-6-yl)methyl][1,1'-biphenyl]-2-carboxylic acid; and,

(12) 1,6-dihydro-1,2-dimethyl-5-propyl-6-[(2'-{(N-benzoyl)sulfonamido}{1,1'-biphenyl}-4-yl) methyl]imidazo[4,5-d]imidazole.

Another class of compounds representative of this embodiment are those wherein:

A—B—C together are:
(a) —C($R^{7a}$)=C($R^{7b}$)—Y—;
(b) —Y—C($R^{7a}$)=C($R^{7b}$)—;

Y is O or S;

$R^{7a}$ and $R^{7b}$ are independently:
(a) H;
(b) $CO_2R^4$
(c) $CON(R^4)_2$;
(d) halo (Cl, Br, F, I);
(e) $C_1$-$C_6$-alkyl optionally substituted with OH, $CO_2R^4$, $N(R^4)_2$, or $CON(R^4)_2$;
(f) aryl or aryl-$C_1$-$C_4$-alkyl where the aryl is optionally substituted with H, halo, $C_1$-$C_4$-alkyl, hydroxy-$C_1$-$C_4$-alkyl, $C_1$-$C_4$-alkoxy, or $CO_2R^4$;
(g) $CF_3$.

Illustrative compounds within this class are:

(1) 2-butyl-3-[(2'-carboxy{1,1'-biphenyl}-4-yl) methyl]-3H-thieno[2,3-d]imidazole-5-carboxylic acid methyl ester;

(2) 2-butyl-3-[(2'-{1H-tetrazol-5-yl}{1,1'-biphenyl}-4-yl)methyl]-3H-thieno[2,3-d]imidazole-5-carboxylic acid methyl ester;

(3) 6-methyl-2-propyl-3-[(2'-{1H-tetrazol-5-yl}{1,1'-biphenyl}-4-yl)methyl]-3H-thieno[2,3-d]imidazole-5-methanol;

(4) 2-butyl-6-methyl-3-[(2'-{1H-tetrazol-5-yl}{1,1'-biphenyl}-4-yl)methyl]-3H-thieno[2,3-d]imidazole-5-carboxylic acid;

(5) 2-butyl-1-[(2'-carboxy{1,1'-biphenyl}-4-yl) methyl]-1H-thieno[2,3-d]imidazole-5-carboxylic acid methyl ester;

(6) 2-butyl-1-[(2'-{1H-tetrazol-5-yl}{1,1'-biphenyl}-4-yl)methyl]-1H-thieno[2,3-d]imidazole-5-carboxylic acid methyl ester; and (7) 2-butyl-1-[(2'-{(N-phenylsulfonyl) carboxamido}{1,1'-biphenyl}-4-yl)methyl]-1H-thieno[2,3-d]imidazole-5-carboxylic acid methylester.

Another class of compounds representative of this embodiment are those wherein:

A—B—C together are:
(a) —N=C($R^{7a}$)—Y—;
(b) —Y—C($R^{7a}$)=N—;
(c) —C($R^{7a}$)=N—Y—;
(d) —Y—N=C($R^{7a}$)—;
(e) =C($R^{7a}$)—Y—N=;
(f) =N—Y—C($R^{7a}$)=;

Y is O or S, $R^{7a}$ is:
(a) H;
(b) $CON(R^4)_2$;
(c) $C_1$-$C_6$-alkyl optionally substituted with OH, $CO_2R^4$, $N(R^4)_2$, or $CON(R^4)_2$;
(d) aryl or aryl-$C_1$-$C_4$-alkyl where the aryl moiety is optionally substituted with H, halo, $C_1$-$C_4$-alkyl, hydroxy-$C_1$-$C_4$-alkyl, $C_1$-$C_4$-alkoxy, or $CO_2R^4$;
(e) $CF_3$.

Illustrative compounds within this class are:

(1) 5-butyl-3-methyl-6-[(2'-{1H-tetrazol-5-yl}{1,1'-biphenyl}-4-yl)methyl]-6H-imidazo[4,5-c]isothiazole;

(2) 5-propyl-4-[2'-{1H-tetrazol-5-yl}{1,1'-biphenyl}-4-yl)methyl]-4H-imidazo[4,5-c]isothiazole;

(3) 5-butyl-6-[2'-{1H-tetrazol-5-yl}{1,1'-biphenyl}-4-yl)-methyl]-6H-imidazo[4,5-d]thiazole-2-methanol;

(4) 4'-[(2-methyl-5-propyl-6H-imidazo[4,5-d]oxazo1-6-yl)-methyl][1,1'-biphenyl]-2-carboxylic acid;

(5) 5-butyl-3-methyl-6-[(2'-{1H-tetrazol-5-yl}-{1,1'-biphenyl}-4-yl)methyl]-6H-imidazo [4,5-d]isothiazole; and, (6) 5-butyl-3-methyl-4-[(2'-{1H-tetrazol-5-yl}-{1,1'-biphenyl}-4-yl)methyl]-4H-imidazo [4,5-d]isothiazole.

Another class of compounds representative of this embodiment are those wherein:

A—B—C together are:
(a) —C(=O)—O—C($R^{7c}$)($R^{7d}$)—;
(b) —C($R^{7c}$)($R^{7d}$)—O—C(=O)—;

$R^{7c}$ and $R^{7d}$ are independently H, alkyl or substituted alkyl, aryl, substituted aryl or substituted aryl-$C_1$-$C_4$-alkyl, wherein substituents can be H, halo, $C_1$-$C_4$-alkyl, hydroxy-$C_1$-$C_4$-alkyl, $CO_2R^4$, or $COR^4$.

Illustrative compounds within this class are:

(1) 2-butyl-1,6-dihydro-6,6-dimethyl-1-[(2'-{1H-tetrazol-5-yl}{1,1'-biphenyl}-4-yl)methyl]-4H -furo[3,4-d]-imidazol-4-one; and, (2) 3-[(2'-carboxy{1,1'-biphenyl}-4-yl)methyl]-3, 6-dihydro-6,6-dimethyl-2-propyl-4H-furo-[3,4-d]imidazol-4-one;

Another class of compounds representative of this embodiment those wherein:

A—B—C together are
(a) —C(=O)—N($R^8$)—C($R^{7c}$)($R^{7d}$)—;
(b) —C($R^{7c}$)($R^{7d}$)—N($R^8$)—C(=O)—;

$R^{7c}$ and $R^{7d}$ and $R^8$ are independently H, alkyl or substituted alkyl, aryl, substituted aryl or substituted aryl-$C_1$-$C_4$-alkyl, wherein substituents can be H, halo, $C_1$-$C_4$-alkyl, hydroxy-$C_1$-$C_4$-alkyl, $CO_2R^4$, or $COR^4$.

Illustrative compounds within this class are:

(1) 2-butyl-5,6-dihydro-6,6-dimethyl-1-[(2'-{1H-tetrazol-5-yl}{1,1'-biphenyl}-4-yl)methyl]pyrrolo[3,4-d]-imidazol-4(1H)-one;

(2) 3-[(2'-carboxy[1,1'-biphenyl]-4-yl)methyl]-5,6-dihydro-6,6-dimethyl-2-propylpyrrolo-[3,4-d]imidaol-4(3H)-one; and (3) 5-butyl-3-methyl-4-[(2'-{(N-acetyl) sulfonamido}{1,1'-biphenyl}-4-yl)methyl]-4H-imidazol[4,5-d]isothiozole.

Illustrative of the substituted imidazo-fused heterocycles of the invention, which are substituted at various positions, are those such as:

(a) imidazo[4,5-d]imidazole, 1,4-dihydro (b) imidazo[4,5-d]imidazole, 1,6-dihydro
(c) 4H-imidazo[4,5-d]thiazole
(d) 6H-imidazo[4,5-d]thiazole
(e) 4H-imidazo[4,5-d]oxazole
(f) 6H-imidazo[4,5-d]oxazole
(g) imidazo[4,5-c]pyrazole, 1,4-dihydro
(h) imidazo[4,5-c]pyrazole, 1,6-dihydro
(i) imidazo[4,5-c]pyrazole, 2,4-dihydro
(j) imidazo[4,5-c]pyrazole, 2,6-dihydro
(k) 4H-imidazo[4,5-c]isoxazole
(l) 6H-imidazo[4,5-c]isoxazole
(m) 4H-imidazo[4,5-c]isothiazole
(n) 6H-imidazo[4,5-c]isothiazole
(o) 4H-imidazo[4,5-d]isoxazole
(p) 6H-imidazo[4,5-d]isoxazole
(q) 4H-imidazo[4,5-d]isothiazole
(r) 6H-imidazo[4,5-d]isothiazole
(s) 1H-thieno[3,4-d]imidazole
(t) 1H-furo[3,4-d]imidazole
(u) imidazo[4,5-d]-1,2,3-triazole, 1,4-dihydro
(v) imidazo[4,5-d]-1,2,3-triazole, 1,6-dihydro
(w) imidazo[4,5-d]-1,2,3-triazole, 2,4-dihydro
(x) imidazo[4,5-d]-1,2,3-triazole, 2,6-dihydro
(y) 4H-imidazo[4,5-c]-1,2,5-thiadiazole
(z) 1H-thieno[2,3-d]imidazole
(aa) 3H-thieno[2,3-d]imidazole
(bb) 1H-furo[2,3-d]imidazole
(cc) 3H-furo[2,3-d]imidazole
(dd) pyrrolo[3,4-d]imidazole, 1,5-dihydro The compounds of Formula (I) can be synthesized using the reactions and techniques described hereinbelow. The reactions are performed in a solvent appropriate to the reagents and materials employed and suitable for the transformation being effected. It is understood by those skilled in the art of organic synthesis that the functionality present on the heterocycle and other parts of the structure should be consistent with the chemical transformations proposed. Depending upon the reactions and techniques employed, this may involve changing the order of synthetic steps, the use of required protecting groups followed by deprotection, and, depending upon the particular imidazo-fused 5-membered heterocycle being formed, the use of different strategies may be employed regarding the cyclization steps and the particular starting material utilized.

The starting materials for preparing the compounds of this invention are dependent upon the nature of the heterocycle being formed. In many cases the heterocycles can be prepared either from a suitably functionalized 5-membered heterocycle by a ring closure step which gives an imidazo fused bicyclic ring system (see Reaction Schemes 1-4) or by starting with a suitably functionalized substituted imidazole and ring closing to give an imidazo-fused 5-membered ring heterocycle (see Reaction Schemes 5-7). The particular route chosen depends upon the nature of the bicyclic ring system being formed and the availability of starting materials.

ABBREVIATIONS USED IN REACTION SCHEMES

| Reagents: | |
|---|---|
| NBS | N-bromosuccinimide |
| AIBN | Azo(bis)isobutyronitrile |
| DDQ | Dichlorodicyanoquinone |
| Ac₂O | acetic anhydride |
| TEA | triethylamine |

-continued

| | |
|---|---|
| DMAP | 4-dimethylaminopyridine |
| PPh₃ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| Me₃SnCl | trimethyltannyl chloride |
| Et₃P | triethylphosphine |
| PPA | polyphosphoric acid |
| TBDMS-Cl | t-butyldimethylsilyl chloride |
| (i-Bu)₂AlH | diisobutylaluminum hydride |
| DBU | 1,8-diazabicyclo[5.4.0]undec-7-ene |
| Et₃N | triethylamine |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Et₂O | diethyl ether |
| Others: | |
| rt | room temperature |
| TBDMS | t-butyldimethylsilyl |
| OTf | OSO₂CF₃ |
| OTs | OSO₂-(4-methyl)phenyl |
| OMs | OSO₂CH₃ |
| Ph | phenyl |
| FAB-MS (FABMS) | Fast atom bombardment mass spectroscopy |
| NOE | Nuclear Overhauser Effect |
| SiO₂ | silica gel |
| trityl | triphenylmethyl |

One approach (Reaction Scheme 1) starts with monocyclic derivatives bearing vicinal carbon bound nitro and amino functions, such as 2 which are often readily available, or can be prepared from the mono nitro derivatives 9 by reaction with hydroxylamine. Compounds 2 may be reduced by any one of several methods, including catalytic hydrogenation or reaction with $SnCl_2$ to give the diamino derivative 3. Such derivatives are often unstable and can be ring-closed to the imidazo fused heterocycle 4 (E=single bond) by reaction with an appropriate carboxylic acid, nitrile, imidate ester, thioimidate ester, amidine, or orthoformate, either neat, or in a solvent appropriate and compatible with the starting materials and reagents, such as polyphosphoric acid, ethanol, methanol, hydrocarbon solvents and with a catalytical amount of acid if required.

Another possible approach, not shown in Reaction Scheme 1, to compounds having the general structure 4 (E=single bond) from 3 involves the reaction of 3 with an appropriate aldehyde in the presence of an oxidizing agent such as $Cu^{II}$, nitrobenzene, or dicyanodichloroquinone (DDQ) to give heterocycles such as 4.

Ring closure of the vicinal diamino heterocycles 3, to give derivatives such as 5 can be effected by treatment with reagents such as $CS_2$, $CSCl_2$, $COCl_2$, $NH_2CONH_2$, alkyl chloroformate, dialkyl carbonates, or potassium cyanate in the presence of bases such as KOH or $K_2CO_3$. Another potential route to 5 (E=O) involves the use of a vicinal amino carboxylate such as 6a or 6b which can be converted to 5 via a Curtius or Hofmann rearrangement on suitable derivatives of 6a/6b such as acyl azides, hydroxyamides or N-haloamides. The bicyclic derivatives 5 can be alkylated under the appropriate conditions with alkyl halides, alkyl mesylates, alkyl tosylates, trialkyloxonium salts or with diazomethane to afford compounds of type 4 (E=O or S).

Another approach to 4 (E=single bond) which has been used for example when A—B—C together are —N=C(CH₃)—N(CH₃)— starts from 2 and utilizes acylation of the amino function with an acyl chloride or anhydride to give the nitro amido compound 7.

such as Cl, Br, I, O-mesyl, or O-tosyl) in one of several ways. One way is to initially form the alkali metal salt of 4 by using MH (where M is Li, Na or K) in anhydrous dimethylformamide (DMF) or by treating 4 with a metal alkoxide such as sodium or potassium methoxide, ethoxide or t-butoxide in an appropriate alcohol such as methanol, ethanol or t-butanol as solvent. The alkylation is then carried out by dissolving the above-mentioned salt of 4 in an anhydrous aprotic solvent such as

REACTION SCHEME 1

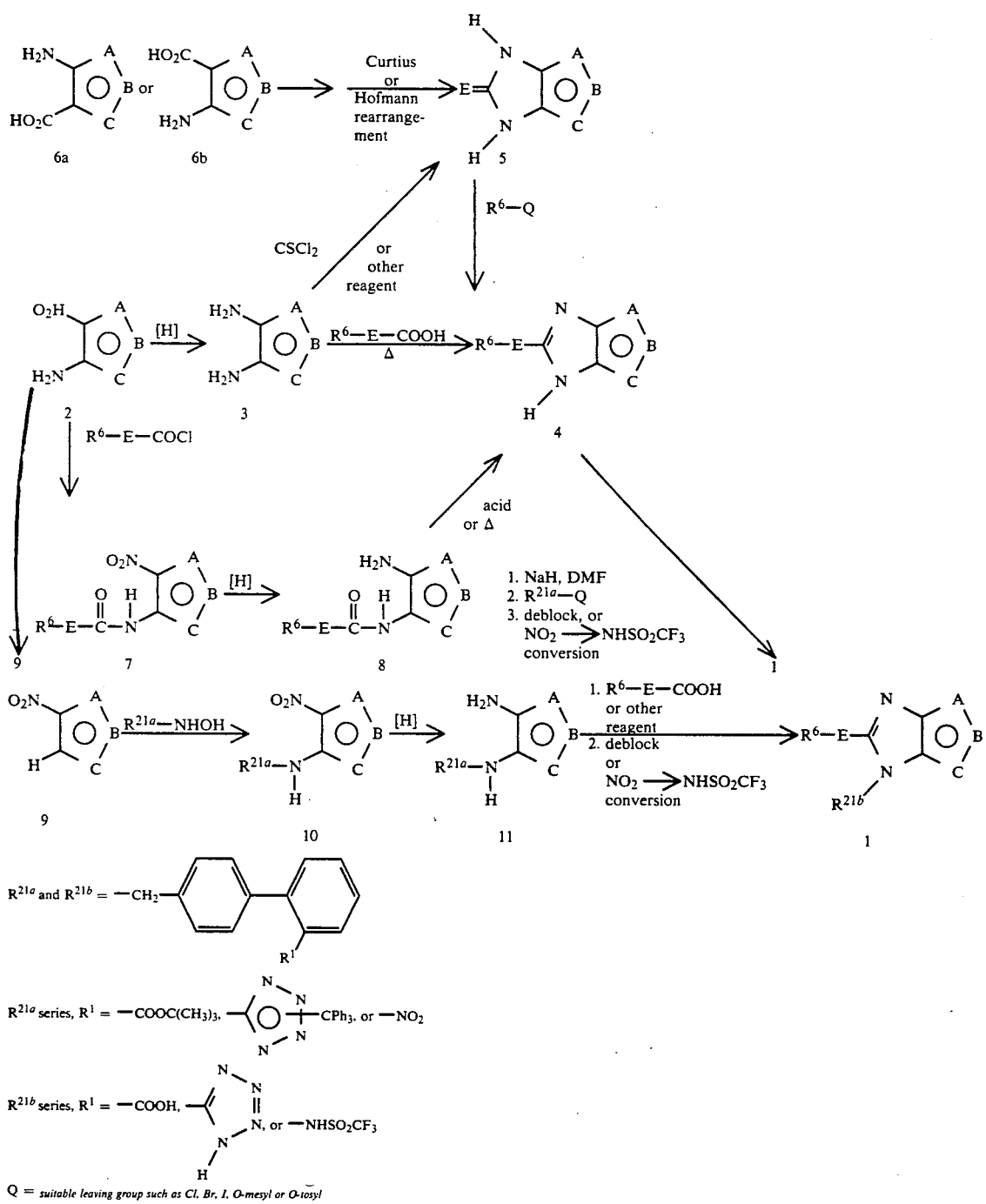

Reduction of the nitro group leads to 8 and this can be ring closed to 4 via cyclodehydration, by heating and-/or acid catalysis.

The imidazo fused heterocycle 4 can then be alkylated with $R^{21a}$-Q (where Q is a suitable leaving group DMF, dimethylsulfoxide (DMSO) or tetrahydrofuran (THF) and reacting it with the alkylating agent $R^{21a}$-Q (preparation of $R^{21a}$-Q is described hereinbelow) at 20° C. to reflux temperature of the solvent for 1 to 24 hours.

If the substituents on the heterocyclic ring system result in an unsymmetrical heterocycle, then the alkylation may produce a mixture of regioisomers. These regioisomers possess distinct physico-chemical and biological properties and in most cases can be separated and purified using conventional separation techniques such as chromatography and/or crystallization. In those cases where the separation of regiosomers is difficult by conventional methods, the mixture can be transformed into suitable derivatives that are more amenable to the usual separation methods. The identification of the individual regioisomers can be made using Nuclear Overhauser Effect (NOE) NMR methods, $^{13}$C NMR methods (e.g. vicinal $^{13}$C-$^1$H coupling constants) or by single crystal X-ray crystallography.

It should be noted that the relative amounts of the regioisomers formed in the alkylation reaction can be influenced by several factors including the nature of the base used (while the alkali metal salt of the heterocycle is generally used, the regioisomeric ratio can be altered in some instances by using the heterocycle in the presence of a weaker base such as triethylamine, diisopropylethylamine, potassium carbonate or sodium bicarbonate) and the nature of the solvent used in the reaction.

The final step in the preparation is the deprotection of the acid moiety on the $R^{21a}$ side-chain or, when $R^1=NO_2$, the conversion of $-NO_2$ to $-NHSO_2CF_3$. In the case of $R^1=-COOH$, the protecting group is usually the t-butyl ester which is removed with trifluoroacetic acid and in the case of $R^1=$tetrazol-5-yl, the protecting group is usually the triphenylmethyl (trityl) group which is removed with aqueous acetic acid under heating. When $R^1=NO_2$, the nitro group is reduced to $R^1=NH_2$ using catalytic hydrogenation, $SnCl_2$, or other reducing agents and then is reacted with trifluoromethylsulfonic anhydride to give the trifluoromethylsulfonamide derivative 1 ($R^1=-NHSO_2CF_3$).

An alternative approach, also shown in Reaction Scheme 1, starts with the mono nitro derivative 9. This can be reacted with a substituted hydroxylamine bearing the $R^{21a}$ side chain, in a manner analogous to the conversion of 9 to 2 for the unsubstituted hydroxylamine, to give 10. Reduction of the nitro function gives the vicinal substituted diamine 11 which can be ring closed in the usual fashion. This allows for regioselective introduction of the $R^{21a}$ side chain into the bicyclic system and the final conversion of 1 ($R^{21a}$) to the required final product 1 ($R^{21b}$) can be carried out as described above.

Another approach to the compounds of this invention is shown in Reaction Scheme 2. In this instance, a monoamino heterocycle such as 12 can be acylated under standard conditions to give the amido derivative 13. This amido compound can be reduced with LiAlH$_4$ in a anhydrous solvent such as THF or Et$_2$O to the alkylamino derivative 14 which can then be nitrosated with isoamyl nitrite to give 15. Such alkylamino nitroso derivatives particularly, for example, when A—B—C together are $-C(CH_3)=N-N(CH_3)-$, undergo cyclodehydration when heated in pyridine to give the imidazo fused bicyclic heterocycle 4. The conversion of 4 to 1 can be carried out as described in Reaction Scheme 1. Alternatively, it should be possible to alkylate 15 prior to ring closure to give the bis-N-alkylated derivative 16 which can then be subjected to cyclodehydration in hot pyridine to give the blocked 1. Separation of any regioisomers that may be formed can be effected by using conventional chromatographic methods, which can be followed by deblocking (or, when $R^1=NO_2$, conversion of $R^1=NO_2$ to $R^1=NHSO_2CF_3$), carried out in the usual fashion.

An alternative approach to the synthesis of 16 might utilize alkylation of the monoalkylated side-chain 14 with $R^{21a}$-Q. This would provide the bis-N-alkylated derivative 17 which can be nitrosated with isoamyl nitrite to give 16.

An additional approach to the compounds of this invention is shown in Reaction Scheme 3. In this approach the starting material is a vicinal bromo nitro heterocycle 18 which is reacted with an appropriate mono alkylamine to give 19. Ring closure can be effected using MeOH/NaOH with heating to give the N-oxide derivative 20 which can be reduced with either triethylphosphine, TiCl$_2$ or Si$_2$Cl$_6$ to give the imidazofused bicyclic heterocycle 4. This can be converted to 1 in the usual fashion as described above in Reaction Scheme 1.

Alternatively, 18 can be reacted with the appropriate dialkylamine to give 22 (which can also be prepared by alkylation of 19 with $R^{21a}$-Q under the appropriate conditions). Ring closure of 21 in a fashion similar to that described above in the conversion of 19 to 20 followed by reduction, separation of the products and deblocking (or conversion of $R^1=NO_2$ to $R^1=NHSO_2CF_3$ as described earlier) gives the required 1.

Another approach to compounds of the Formula 1 (particularly where A—B—C together are $-C(R^{7a})=C(R^{7b})-S-$) is shown in Reaction Scheme 4. In these instances, the starting material is the substituted heterocycle 23 which can be alkylated with $R^{21a}$-Q to give 24. Treatment with hydrazine/nitrous acid and a refluxing alcohol gives rise to 25 via a Curtius rearrangement on the intermediate acyl azide. The cyclization of 25 can be accomplished with polyphosphoric acid or other acidic catalyst and final transformation to 1 can be effected by deblocking (if necessary) or the conversion of $R^1=NO_2$ to $R^1=NHSO_2CF_3$ as described earlier.

REACTION SCHEME 2

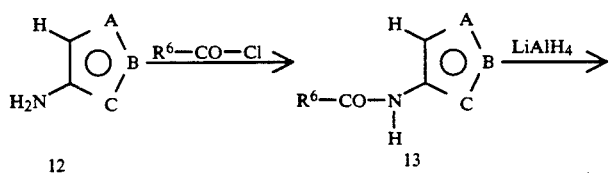

12     13

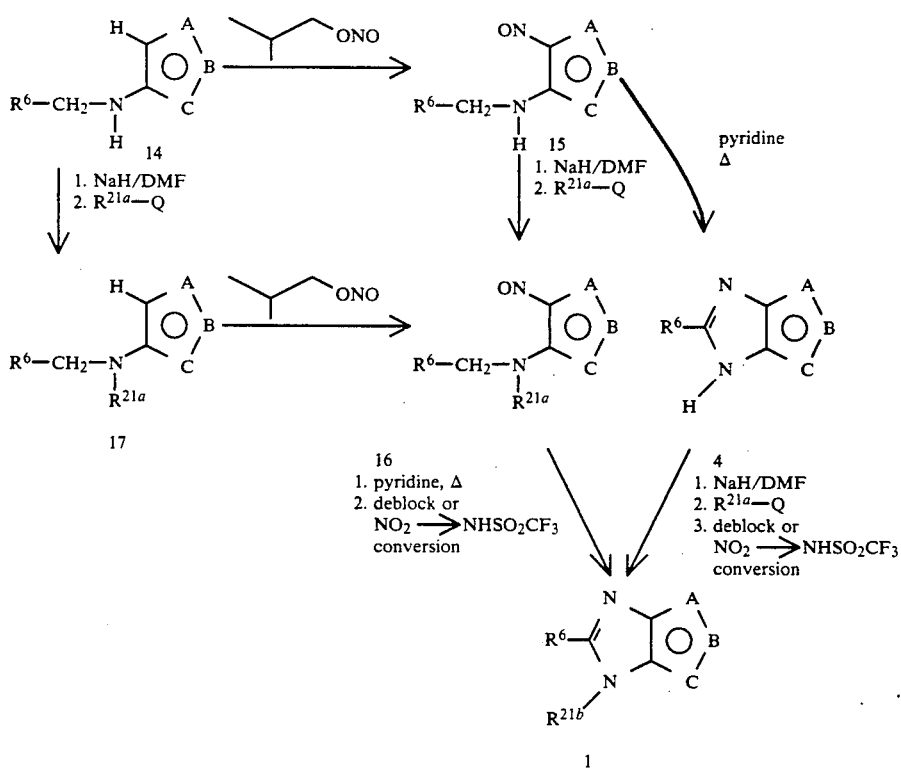

REACTION SCHEME 3

REACTION SCHEME 4

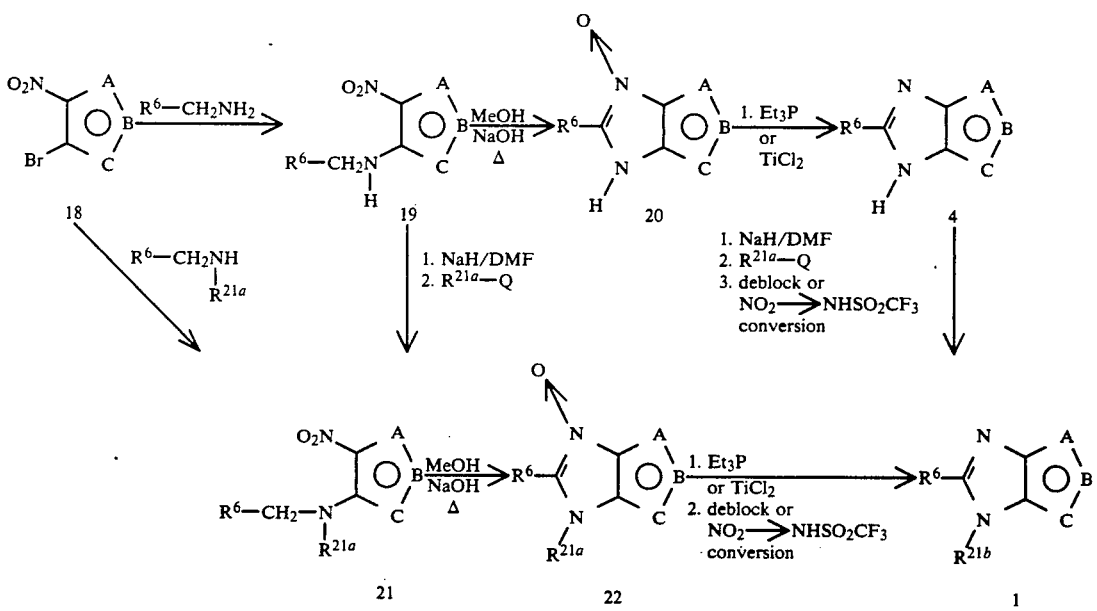

The required heterocyclic precursors for these transformations which are shown in Reaction Schemes 1-4 may be prepared by adaptations of literature procedures. A listing of representative precursors to these imidazo fused bicyclic heterocycles, along with literature references to their preparations is shown below in Table 1.

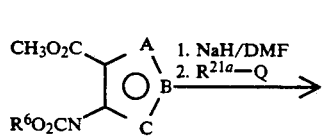

21
-continued
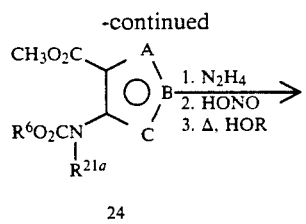
24
22
-continued
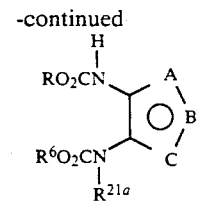
25
1. PPA
2. deblock or
   $NO_2 \rightarrow NHSO_2CF_3$
   conversion
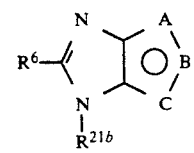
1
TABLE 1
| Structure | Name | Reference |
|---|---|---|
| 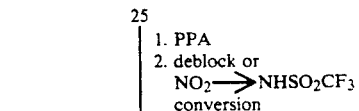 | 5-amino-1-methylimidazole | J. Chem. Soc., 2028(1948) |
| 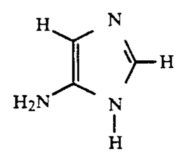 | 5-aminoimidazole | Can. J. Res., 19B 296(1941) |
| 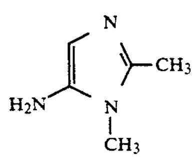 | 5-amino-1,2-dimethyl-imidazole | J. Chem. Soc, 1648(1954) |
| 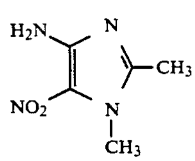 | 4-amino-5-nitro-1,2-dimethylimidazole | J. Het. Chem. 6, 53(1969) |
| 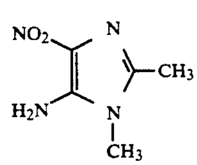 | 5-amino-4-nitro-1,2-dimethylimidazole | J. Het. Chem. 6, 53(1969) |
| 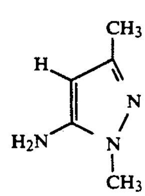 | 5-amino-1,3-dimethylpyrazole | U.S. Pat. No. 3,646,059 |

TABLE 1-continued

| Structure | Name | Reference |
|---|---|---|
| (5-amino-3-methylpyrazole structure) | 5-amino-3-methylpyrazole | U.S. Pat. No. 3,646,059 |
| (4,5-diamino-1-methyl-3-phenylpyrazole structure) | 4,5-diamino-1-methyl-3-phenylpyrazole | J. Gen Chem. (USSR) 32, 1898(1962) |
| (3-nitro-1,5-dimethylpyrazole structure) | 3-nitro-1,5-dimethylpyrazole | J. Gen Chem. (USSR) 50, 2106(1908) |
| (3,4-diamino-1,5-dimethylpyrazole structure) | 3,4-diamino-1,5-dimethylpyrazole | J. Gen Chem. (USSR) 50, 2106(1908) |
| (4-nitro-1,3-dimethylpyrazole structure) | 4-nitro-1,3-dimethylpyrazole | J. Gen. Chem. (USSR) 50, 2106(1980) |
| (5-amino-3-methylisoxazole structure) | 5-amino-3-methyl-isoxazole | J. Het. Chem. 10, 181(1973) |
| (4,5-diamino-3-methylisoxazole structure) | 4,5-diamino-3-methylisoxazole | J. Het. Chem. 10, 181(1973) |
| (4-butyramidothiazole structure, C$_3$H$_2$CONH) | 4-butyramidothiazole | Eur. J. Med. Chem. 14 105(1979) |
| (5-nitro-2-methylthiazole structure) | 5-nitro-2-methylthiazole | J. Org. Chem. 33 2545(1968) |
| (4-nitro-2-methylthiazole structure) | 4-nitro-2-methylthiazole | J. Org. Chem. 33 2545(1968) |

TABLE 1-continued

| Structure | Name | Reference |
|---|---|---|
| 4-aminoisothiazole | 4-aminoisothiazole | J. Chem. Soc., 3061(1959) |
| 4-amino-3-methylisothiazole | 4-amino-3-methylisothiazole | J. Chem. Soc., 3061(1959) |
| 5-amino-3-methylisothiazole | 5-amino-3-methylisothiazole | J. Chem. Soc., 3061(1959) |
| 5-amino-4-nitro-3-methylisothiazole | 5-amino-4-nitro-3-methylisothiazole | J. Chem. Soc., 3061(1959) |
| 3,4-diamino-1,2,5-thiadiazole 1,1-dioxide | 3,4-diamino-1,2,5-thiadiazole 1,1-dioxide | Liebigs Ann. Chem, 4, 337 (1988) |
| 4,5-diamino-1H-1-benzyl-1,2,3-triazole | 4,5-diamino-1H-1-benzyl-1,2,3-triazole | Izv. Akad. Nauk SSSR, Ser Khim, 11, 2633(1985) |
| 2,3-diaminothiophene | 2,3-diaminothiophene | Arch. Pharm (Weinheim), 314, 567(1981) |
| 1-benzyl-3,4-diamino-2H-pyrrol-2-one | 1-benzyl-3,4-diamino-2H-pyrrol-2-one | Liebeigs Ann. Chem, 183, 1424(1978) |
| 4,5-diamino-3-[(phenylmethylene)amino]-2H-pyrrol-2-one | 4,5-diamino-3-[(phenylmethylene)amino]-2H-pyrrol-2-one | Japanese Patent 53/109527 |
| 2,3-diaminomaleimide | 2,3-diaminomaleimide | Chem. Ber., 116, 2591(1983) |

TABLE 1-continued

| Structure | Name | Reference |
|---|---|---|
| $H_2N$—⟨thiophene⟩—$H_2N$ | 3,4-diaminothiophene | Bull Soc. Chem. Fr., 5-6, pt. 2, 153(1983) |
| $H_2N$—⟨thiadiazole⟩—$H_2N$ | 3,4-diamino-1,2,5-thiadiazole | J. Het. Chem, 13, 13(1976) |

In certain cases due to the nature of the heterocycle being prepared and to the availability of starting materials, it may be advantageous to prepare some of the compounds of this invention from a suitably functionalized imidazole ring and then ring closing to give compounds of Formula 1. Some specific examples are shown in Reaction Schemes 5-7. Thus, Reaction Scheme 5 shows an approach to the preparation of the substituted regioisomers of 1H- and 3H-thieno[2,3-d]imidazoles. The substituted imidazole 26 can be readily alkylated in the fashion described earlier by using NaH in DMF, followed by treatment of the anion so formed with the alkylating agent $R^{21a}$-Q to give a separable mixture of the regioisomers 27a and 27b. These can be independently converted to ketones 28a and 28b, respectively, via oxidation with a suitable oxidizing agent such as $MnO_2$ to the aldehyde, followed by reaction with an appropriate Grignard reagent to give the secondary alcohol which is further oxidized with $MnO_2$ to 28a, b. These isomers can then be independently converted to the corresponding thieno[2,3-d]imidazoles 29 by treatment with a thioglycolic acid ester and the appropriate alkoxide in the appropriate refluxing alcohol (i.e., 28a gives the 3H-thieno-[2,3-d]imidazole 29a and 28b gives the 1H-thieno-[2,3-d]imidazole regioisomer 29b). Compounds 29a,b can be deblocked (or the usual $R^1=NO_2 \rightarrow R^1=NHSO_2CF_3$ conversion effected) to give 33a,b (i.e. 1 where $R^{7a}=R^{22}$ and $R^{7b}=COOR^{23}$). Saponification of 33a,b gives the carboxylic acid 35a,b. Other conversions possible with the 29a,b regioisomers include reduction with $LiAlH_4$ to the alcohol 30a,b, saponification followed by decarboxylation to give 31a,b after deblocking, and conversion of the alkyl carboxylate to a ketone with an alkyl lithium reagent to give 32a,b. It should be noted that in this instance, as well as in the above mentioned 29a,b→30a,b transformation with $LiAlH_4$, alkyl lithium will likely cause concomitant reduction of the $NO_2$ group (if it is present in the $R^{21a}$ moiety) to an $NH_2$ functionality. In these instances, conversion to the trifluoromethylsulfonamide derivative is accomplished using trifluoromethylsulfonic anhydride in the usual fashion. In addition, the intermediate 28a can be utilized as a precursor to the imidazo[4,5-c]pyrazole, 1,6-dihydro series by cyclization with a substituted hydrazine derivative, to give 34a, after deblocking (or the $R^1=NO_2$ to $R^1=NHSO_2CF_3$ conversion). Similarly, 28b can be converted to the imidazo[4,5-c]-pyrazole 1,4-dihydro series 34b.

REACTION SCHEME 5

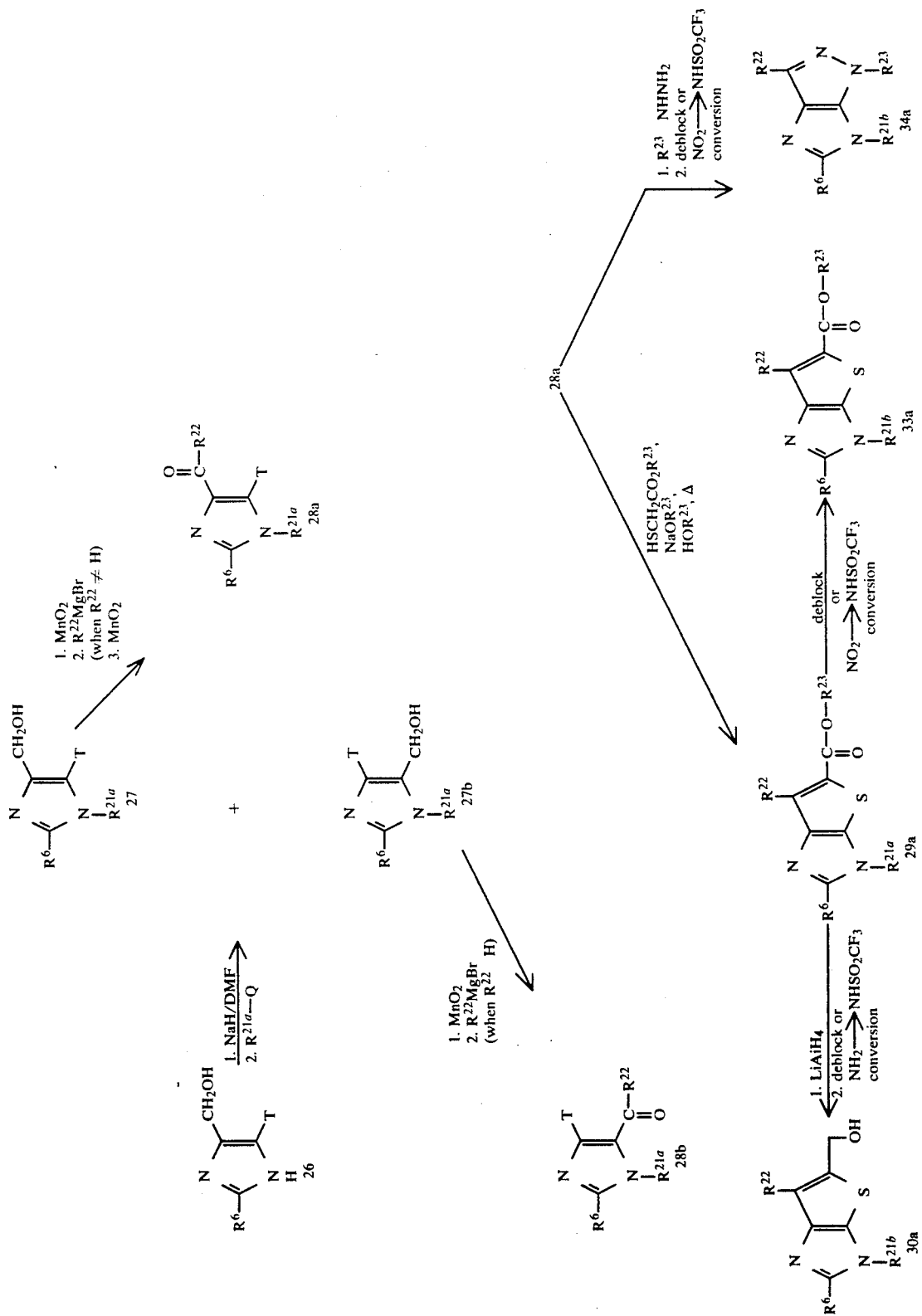

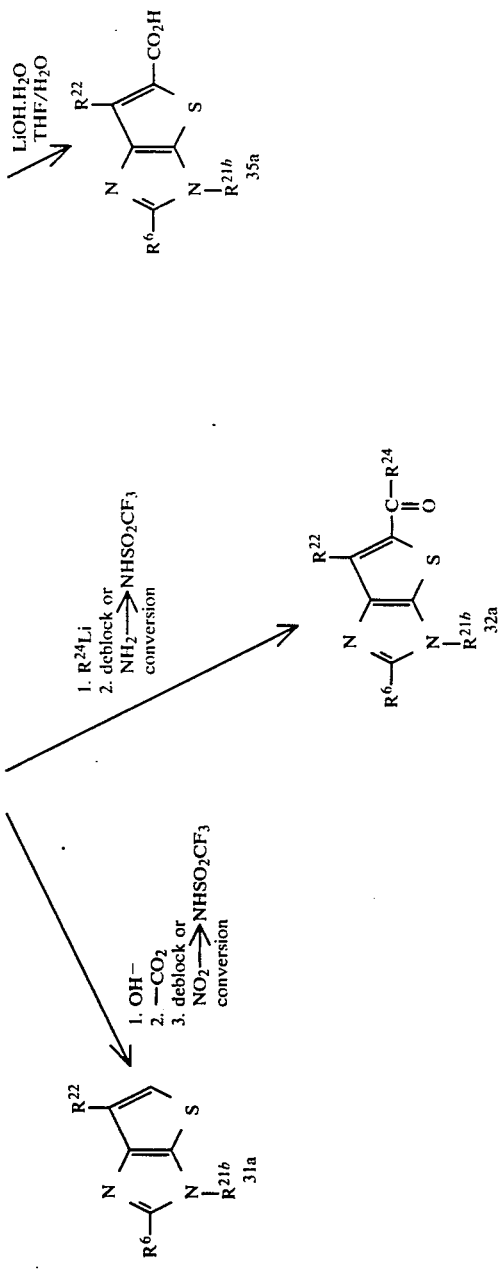

Similarly, 28b can be converted into the regioisomeric 29b, 30b, 31b, 32b, 33b, and 34b.

T=halogen (Cl, Br, F, I)

$R^{22}$=H, alkyl, substituted alkyl, aryl or substituted aryl $R^{23}$=alkyl or substituted alkyl.

$R^{24}$=alkyl or substituted alkyl.

A similar cyclization using hydroxylamine can be used to give the 6H-imidazo[4,5-d]isoxazole series (starting from 28a) or the 4H-imidazo[4,5-d]-isoxazole series (starting from 28b).

Preparation of the lactone derivatives 36a,b can probably be accomplished from the regioisomers 35a,b as shown in Reaction Scheme 6. These tertiary alcohol starting materials can be obtained from respective ketones such as 28a,b (see Reaction Scheme 5) by reaction with an appropriate Grignard reagent, followed by protection of the alcohol with t-butyldimethylsilylchloride. Thus, lithiation of 35a,b can be carried out with t-BuLi and the lithio derivative reacted with methyl chloroformate. The intermediate so formed can be treated with acid to remove the t-butyldimethylsilyl protecting group and to effect cyclization to the lactone. Deblocking (if necessary) and conversion of $R^1=NO_2 \rightarrow R^1=NHSO_2CF_3$ can be effected as described earlier in Reaction Scheme 1.

A possible route to the substituted 1,5-dihydropyrrolo[3,4-d]imidazole 41 is shown in Reaction Scheme 7. Thus, the functionalized imidazole 37 (or its regioisomer) prepared as described in European Patent Application 253,310 can be treated with tosyl chloride in pyridine to give the O-tosylate which can then be converted to the aminomethyl derivative via a Gabriel synthesis (displacement of tosylate with potassium phthalimide, followed by de-phthaloylation with hydrazine). This intermediate can be blocked by treatment with 1,2-bis(chlorodimethylsilyl)ethane to give the intermediate 38. Lithiation and subsequent formylation is accomplished by treatment with butyllithium and DMF to give the intermediate 39 which can cyclize under acid catalysis to the pyrrolo[3,4-d]imidazole derivative 40. Compound 40 is then treated with an alkyl, acyl or sulphonyl halide to block the pyrrole ring nitrogen. Deblocking with acid (or the $R^1=NO_2 \rightarrow R^1=NHSO_2CF_3$ conversion) under the conditions described earlier gives rise to the required 41.

With regard to the preparation of derivatives containing the furo[2,3-d]imidazole heterocycle (i.e., compounds of Formula 1 where A—B—C together are —C($R^{7a}$)=C($R^{7b}$)—O— and —O—C($R^{7a}$)=C($R^{7b}$)—) these can be prepared by alkylation of the appropriate furo[2,3-d]imidazole [prepared as described in Chem. Pap., 40, 675(1986)] using the general procedures shown in Reaction Scheme 1 for the conversion of 4 to 1.

The alkylating agent $R^{21a}$-Q utilized in Reaction Schemes 1-7, including the preferred biphenyl benzylic halides 47a, 47b and 47c as shown in Reaction Scheme 8 can be prepared as described in European Patent Applications 253,310 and 291,969 and the references cited therein. However, a preferred method to prepare the biphenyl precursors 46a, 46b, and 46c using Ni(O) catalyzed cross-coupling reaction [E. Negishi, T. Takahashi, and A. O. King, Org. Synthesis, 66, 67 (1987)] is outlined in Reaction Scheme 8. As shown in Reaction Scheme 8, treatment of 4-bromotoluene 42 with t-BuLi, followed by the addition of a solution of $ZnCl_2$, produces the organo-zinc compound 44.

REACTION SCHEME 6

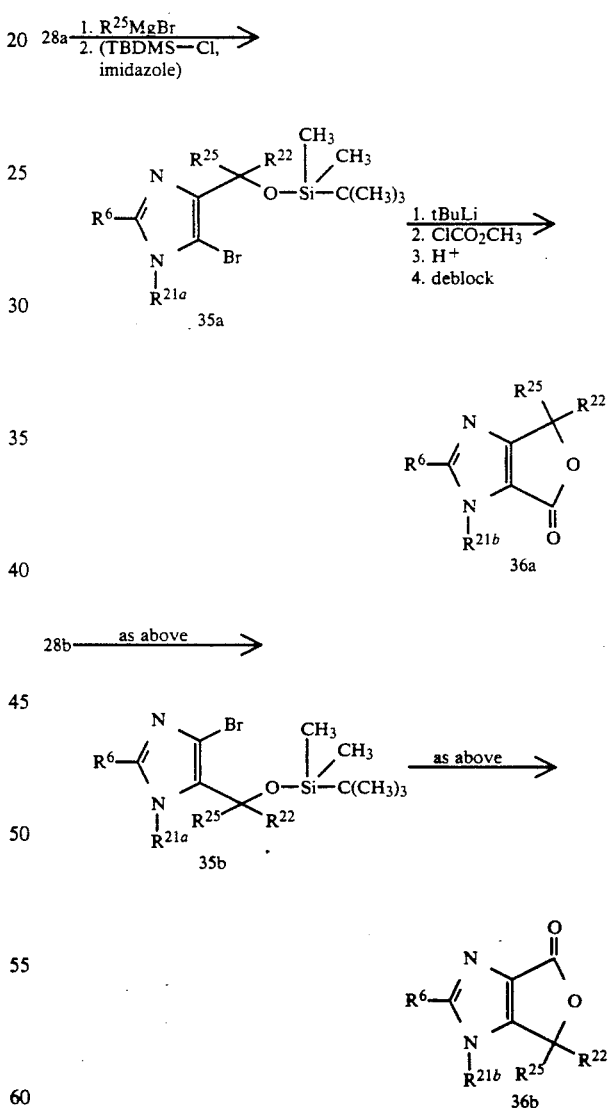

$R^{25}$ = aryl, substituted aryl, alkyl or substituted alkyl $R^{26}$ = —COOtBu; $R^{21b}$ = —COOH TBDMS = t-butyldimethylsilyl

REACTION SCHEME 7

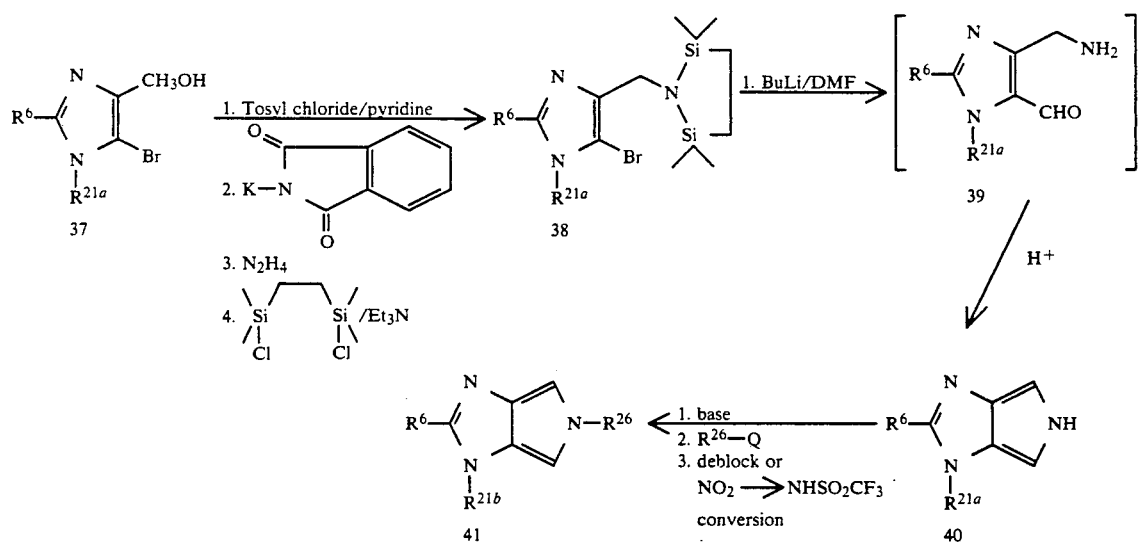

R[26] = alkyl, acyl, or alkylsulphonyl.

Compound 44 is then coupled with 45a or 45b in the presence of Ni(PPh₃)Cl₂ catalyst to produce the desired biphenyl compound 46a or 46b (PPh₃=triphenylphosphine). Similarily, 1-iodo-2-nitrobenzene 45c is coupled with organo-zinc compound 44 in the presence of Pd(PPh₃)₄ catalyst [prepared by treating Cl₂Pd(PPh₃)₂ with (i-Bu)₂AlH (2 equiv.)] to give the biphenyl compound 46c. These precursors, 46a, 46b and 46c, are then transformed into halomethylbiphenyl derivatives 47a, 47b, and 47c, respectively, according to procedures described in European Patent Applications 253,310 and 291,969.

REACTION SCHEME 8

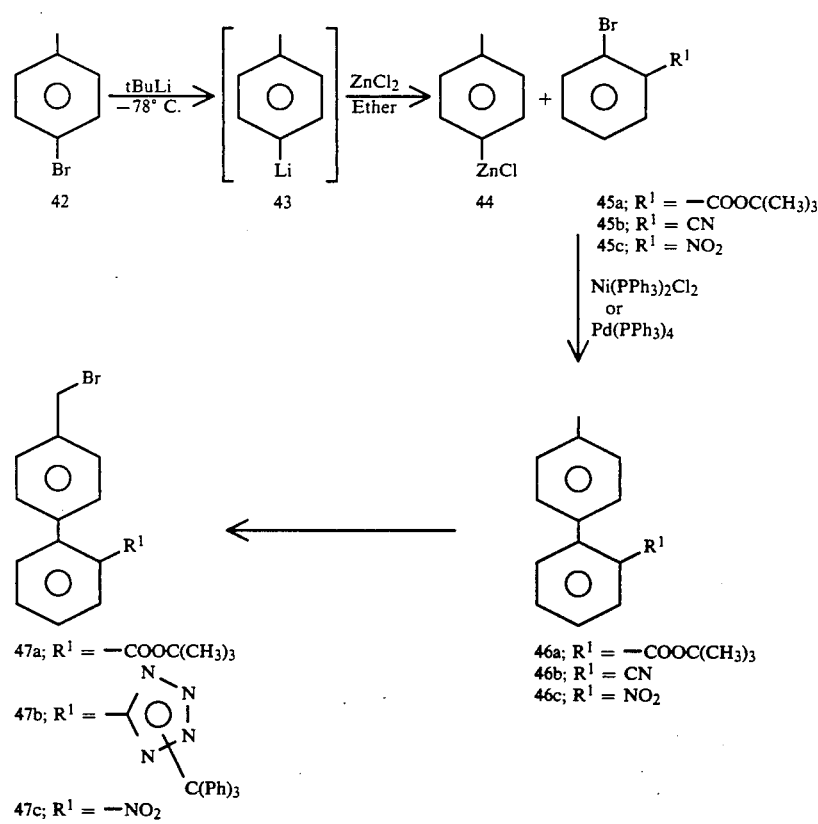

Compounds of formula I where $R^1$ is —CONHSO₂R²¹ (where R²¹=alkyl, aryl or heteroaryl) may be prepared from the corresponding carboxylic acid derivatives (1) as outlined in Scheme 9. The carboxylic acid (2), obtained as described earlier, can be converted into the corresponding acid chloride by treatment with refluxing thionyl chloride or preferably wtih oxalylchloride and a catalytic amount of dimethylformamide at low temperature [A. W. Burgstahler, L. O. Weigel, and C. G. Shaefer-*Synthesis*, 767, (1976)]. The acid chloride then can be treated with the alkali metal salt of $R^{21}SO_2NH_2$ to form the desired acylsulfonamide 48. Alternatively, these acylsulfonamides may be also prepared from the carboxylic acids using N,N-diphenylcarbamoyl anhydride intermediates [F. J. Brown et al— European Patent Application, EP 199543; K. L. Shepard and W. Halczenko- *J. Het. Chem.*, 16, 321 (1979). Preferably the carboxylic acids can be converted into acyl-imidazole intermediates, which then can be treated with an appropriate aryl or alkylsulfonamide and diazabicycloundecane (DBU) to give the desired acyl-sulfonamide 48 [J. T. Drummond and G. Johnson-*Tetra. Lett.*-29, 1653 (1988)].

REACTION SCHEME 9

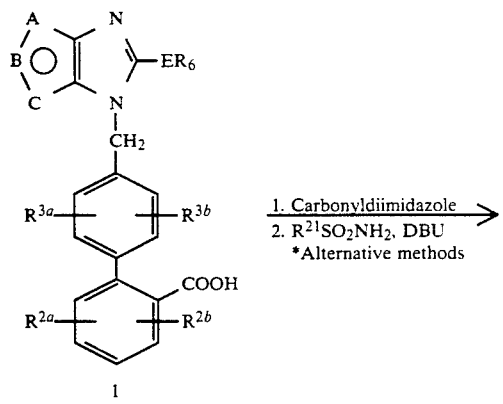

1. Carbonyldiimidazole
2. $R^{21}SO_2NH_2$, DBU
*Alternative methods

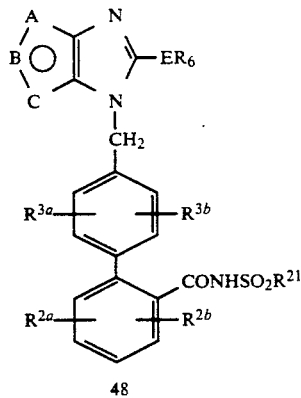

48

*Alternative Methods:
a) (i) $SOCl_2$, reflux (ii) $R^{21}SO_2NH^-M^+$ (where M is Na or Li)
b) (i) $(COCl)_2$—DMF, −20° C. (ii) $R^{21}SO_2NH^-M^+$
c) (i) N(N,N-Diphenylcarbanoyl)pyridinium chloride/Aq. NaOH (ii) $R^{21}SO_2NH^-M^+$

REACTION SCHEME 10

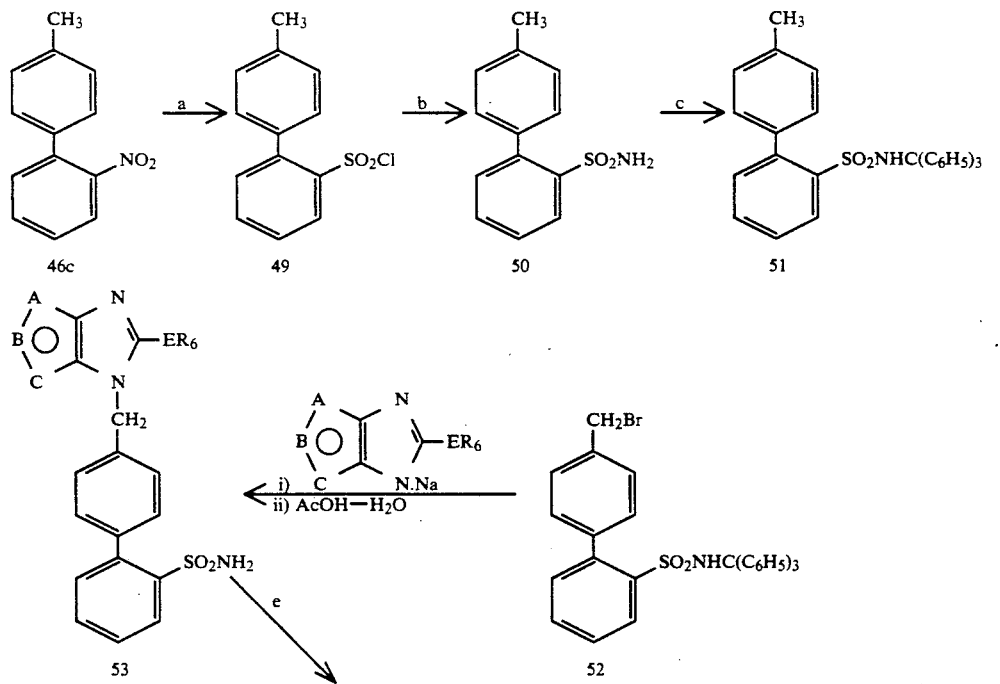

-continued

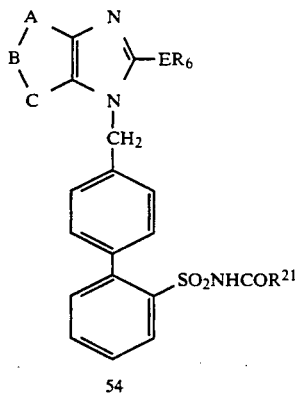

54 a i) H₂/Pd—C, ii) NaNO₂—HCl, iii) SO₂, AcOH, CuCl₂
b NH₃ or (NH₄)₂CO₃
c (C₆H₅)₃CCl, Et₃, CH₂Cl₂, 25° C.
d N-Bromosuccinimide
e R²¹COCl or R²¹CO—Im or other acylating agents Compounds of formula I where $R^1$ is —SO₂NHCOR²¹ may be prepared as outlined in Scheme 10. The nitro compound 46c (prepared as described in Scheme 8) can be reduced to the corresponding amino compound and converted into aromatic diazonium chloride salt, which then can be reacted with sulfur-dioxide in the presence of a copper (II) salt to form the corresponding arylsulfonyl choride 49 [H. Meerwein, G. Dittmar, R. Gollner, K. Hafner, F. Mensch and O. Steifort—Chem. Ber., 90, 841 (1957); A. J. Prinsen and H. Cerfontain, Recueil, 84, 24 (1965); E. E. Gilbert, Synthesis, 3 (1969) and references cited therein]. The sulfonyl chloride can be reacted with ammonia in aqueous solution or in an inert organic solvent [F. H. Bergheim and W. Baker, J. Amer. Chem. Soc., 66, (1944), 1459], or with dry powdered ammonium carbonate, [E. H. Huntress and J. S. Autenrieth, J. Amer. Chem. Soc., 63, (1941), 3446; E. H. Huntress and F. H. Carten, J. Amer. Chem. Soc., 62, 91940), 511] to form the sulfonamide 50. The benzylbromide 52 may be prepared from the sulfonamide 50 as outlined in Scheme 10, and then can be reacted with an alkali metal salt of an appropriate heterocyclic compound to form the key sulfonamide 53. The sulfonamide 53 may be also prepared from the aromatic sulfonyl chloride 57, which may be prepared from the aryl amine 56 as outlined in Scheme 11. The acylation of 53 with appropriate acyl chlorides (or acylimidazoles or other acylating agents) may produce the desired acylsulfonamides 54.

The compounds bearing $R^1$ as —SO₂NHR²¹ (where $R^{21}$ is heteroaryl) may be prepared by reacting the aromatic sulfonyl chloride 57 with appropriate heteroaryl amines as outlined in Scheme 11. The sulfonyl chloride 57 may be the prefered intermediate for the synthesis of this class of compounds. The aromatic sulfonyl chlorides may also be prepared by reacting the sodium salt of aromatic sulfonic acids with PCl₅ of POCl₃ [C. M. Suter, The organic Chemistry or Sulfur, John Wiley & Sons, 459, (1944)] The aromatic sulfonic acid precursors may be prepared by chlorosulfonation of the aromatic ring with chlorosulfonic acid [E. H. Huntress and F. H. Carten, J. Amer. Chem., Soc., 62, 511 (1940)].

REACTION SCHEME 11

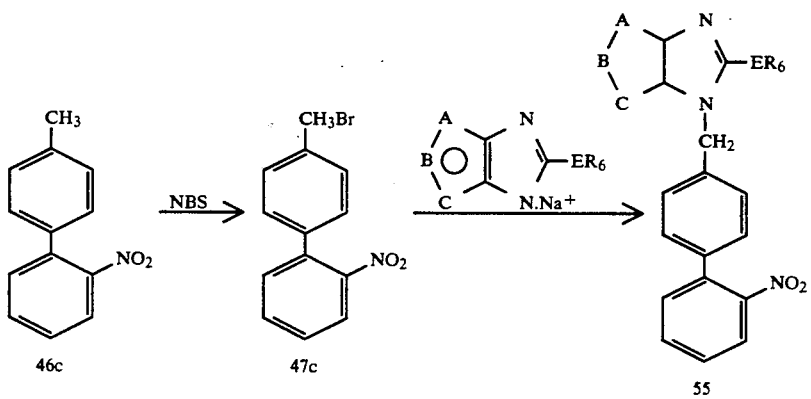

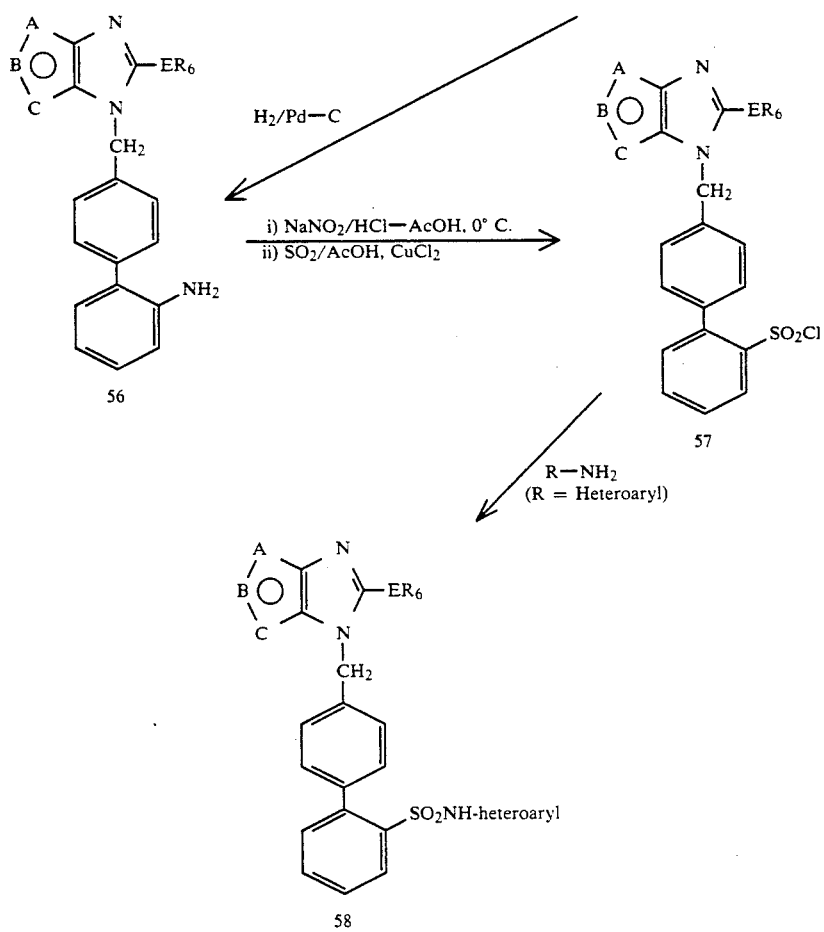

REACTION SCHEME 12

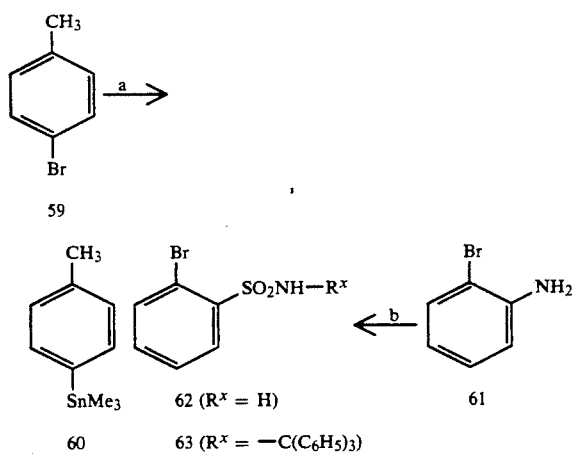

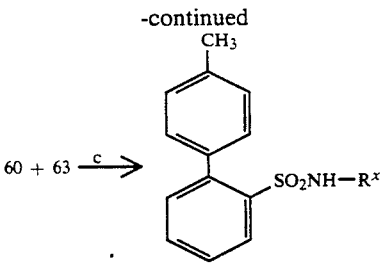

50 ($R^x$ = H)
51 ($R^x$ = —C(C$_6$H$_5$)$_3$)

a (i) t-BuLi/ether, −78° C. (ii) Me$_3$SnCl
b (i) NaNO$_2$/HCl (ii) SO$_2$, CuCl$_2$
c Pd(PPh$_3$)$_4$, Toluene or (PPh$_3$)$_2$PdCl$_2$, DMF, 90° C.

The biaryl sulfonamides 50 and 51 (described in Scheme 10) can be prepared alternatively using palladium(0) catalyzed cross-coupling reactions of appropriate aryl-organotin precursors [J. K. Stille, Pure Appl. Chem., 57, 1771 (1985); T. R. Baiely, Tetra Lett., 27, 4407 (1986)]; D. A. Widdowson and Y. Z. Zhang, Tetrahedron, 42, 2111 (1986)], as outlined in Scheme 12. The organotin compound 60 [S. M. Moerlein, J. Organometallic Chem., 319, 29 (1987)], obtained from the aromatic precursor 59, may be coupled with aryl sulfonamide 63 using Pd(PPh$_3$)$_4$ or (PPh$_3$)$_2$PdCl$_2$ as catalysts to give biaryl sulfonamide 51. Similarly, the benzyl bromide 52 may be alternatively prepared from the appropriate organotin precursor 66 using the Pd(0)

catalyzed cross-coupling reaction as outlined in Scheme 13.

REACTION SCHEME 13

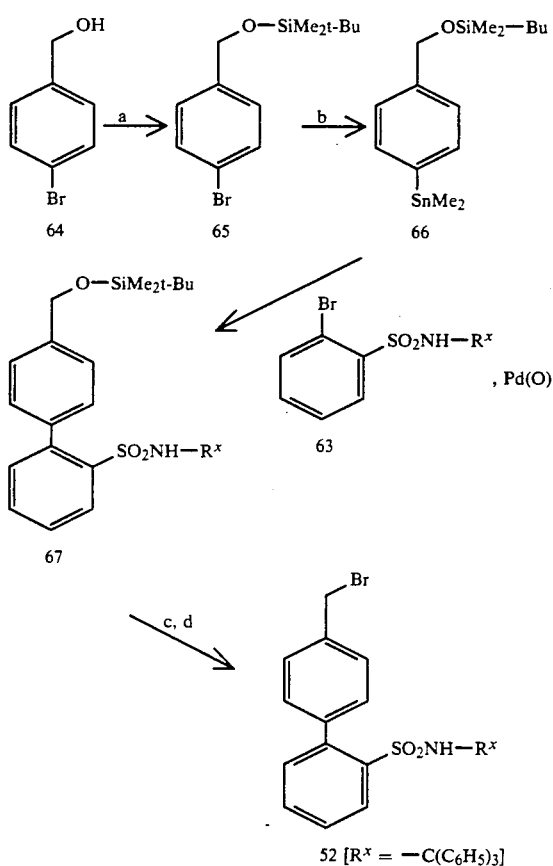

a t-BuMe$_2$Si—Cl/Imidazole, DMF
b t-BuLi. —78° C., Me$_3$SnCl
c Tetrabutylammonium fluoride
d CBr$_4$/Ph$_3$P The compounds bearing $R^1$ as —CH$_2$SO$_2$NHCOR$^{21}$ or —CH$_2$SO$_2$NHR$^{21}$ may be prepared as outlined in Scheme 14. The key precursor aryl-methanesulfonyl chloride 73 may be prepared either from the reaction of aryl-methylmagnesium chloride (72) (obtained sulfuryl-chloride [S. N. Bhattacharya, C. Eaborn and D. P. M. Walton, J. Chem. Soc. C, 1265 (1968)], or by oxidation of the aryl-methylthioacetate (71) (prepared from the benzyl bromide (70) with chlorine in presence of trace amount of water [Bagnay and Dransch, Chem. Ber., 93 784 (1960)]. Alternatively, the aryl-methylthioacetate 71 can be oxidized with sulfuryl chloride in presence of acetic anhydride to form aryl-methylsulfinyl chloride [S. Thea and G. Cevasco, Tetra. Lett., 28, 5193 (1987)], which can be further oxidized with appropriate oxidizing agents to give the sulfonyl chloride 73. In case of compounds 71 and 72, when an additional sulfur bearing group is present either as a constituent of the heteroaromatic giving system or as a substituent on the aromatic and heteroaromatic givings, the sequence of be compatible, and appropriate modifications may be reorganized. The compounds 74 and 75 can be obtained by reacting the sulfonyl chloride 73 with appropriate amines.

Compounds where $R^1$ is —NHSO$_2$NHR$^{21}$ may be prepared by the reaction of appropriate primary amines with the sulfamide 77 [S. D. McDermott and W. J. Spillane, Synthesis, 192 (1983)], as described in Scheme 15. The compound 77 may be obtained from the corresponding N-t-butylsulfamide 76 after treatment with anhydrous trifluoroacetic acid [J. D. Catt and W. L. Matier, J. Org. Chem., 39, 566 (19740], which may be prepared by the reaction of the aromatic amine 56 with t-butylsulfamoyl chloride [W. L. Matier, W. T. Comer and D. Deithchman, J. Med. Chem., 15, 538 (1972)].

REACTION SCHEME 14

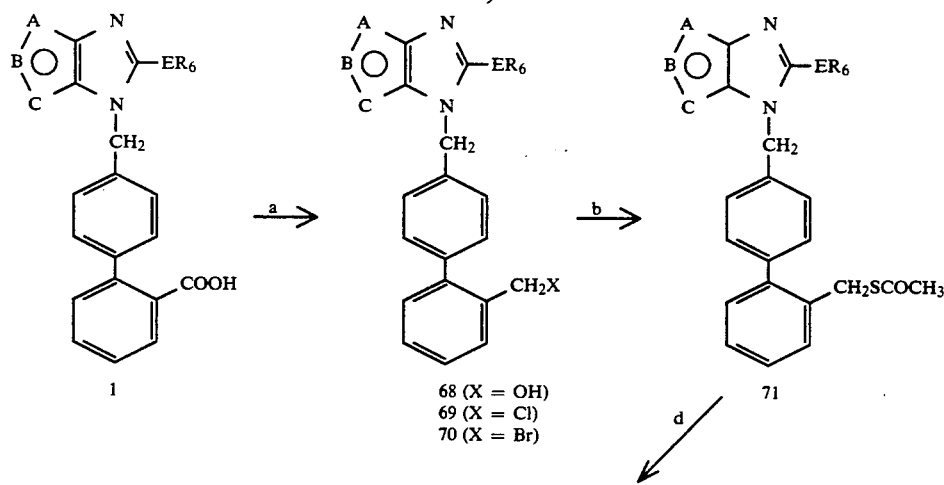

-continued

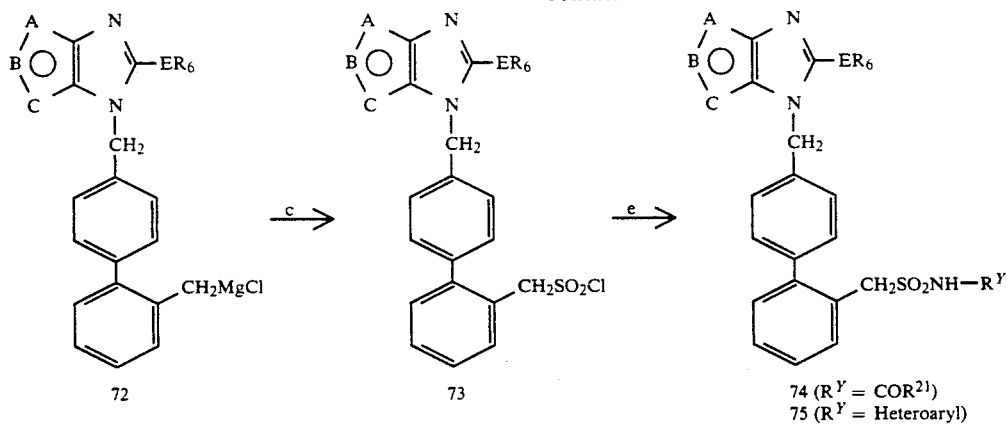

a i) EtOCOCl/Et₃N, THF, 0° C. ii) NaBH₄ iii) CCl₄ or CBr₄/PPh₃
b AcSK
c SO₂Cl₂
d Cl₂, AcOH, H₂O or, i) SO₂Cl₂ ii) oxidation
e R$^Y$NH₂ or, i) NH₃ ii) Acylation

REACTION SCHEME 15

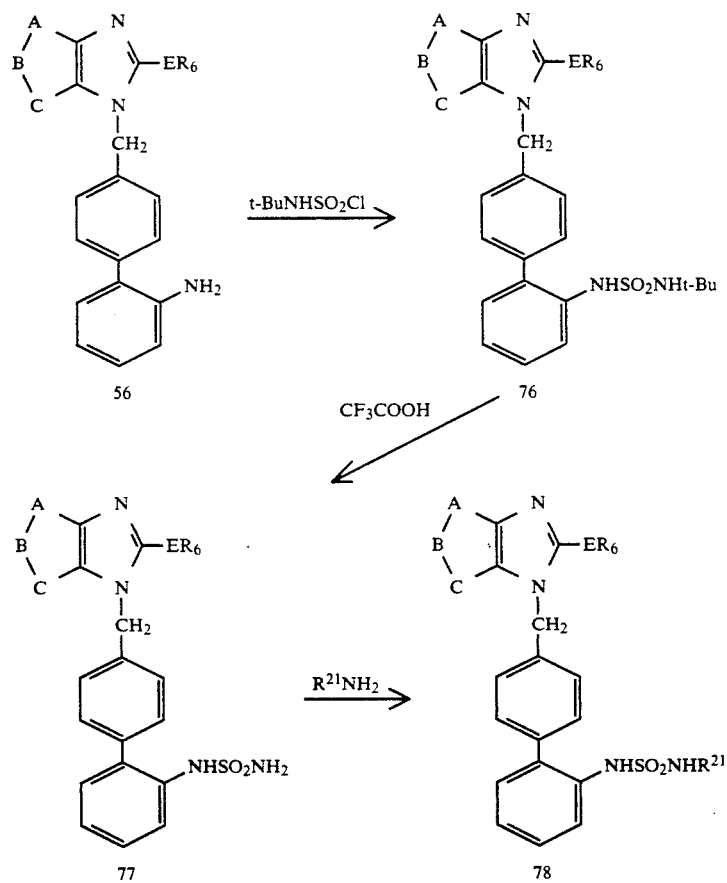

The compounds of this invention form salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H₂SO₄, H₃PO₄, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (A II) is a powerful arterial vasoconstrictor, and it exerts its action by interacting with specific receptors present on cell membranes. The compounds described in the present invention act as competitive antagonists of A II at the receptors. In order to identify A II antagonists and determine their efficacy in vitro, the following two ligand-receptor binding assays were established.

Receptor Binding Assay Using Rabbit Aortae Membrane preparation

Three frozen rabbit aortae (obtained from Pel-Freeze Biologicals) were suspended in 5 mM Tris-0.25M Sucrose, pH 7.4 buffer (50 ml) homogenized, and then centifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential A II antagonist which gives 50% displacement of the total specifically bound $^{125}$I-Sar$^1$Ile$^8$-angiotensin II was presented as a measure of the efficacy of such compounds as A II antagonists.

Receptor Assay Using Bovine Adrenal Cortex Preparation

Bovine adrenal cortex was selected as the source of A II receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 ul) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential A II antagonist which gives 50% displacement of the total specifically bound $^3$H-angiotensin II was presented as a measure of the efficacy of such compounds as A II antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down th spinal column. The rats were immediately placed on a Harvard Rodent Ventilator (rate—60 strokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermistatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention listed below were evaluated and all were found to exhibit an activity of at least $IC_{50} < 50$ $\mu$M thereby demonstrating and confirming the utility of the compounds of the invention as effective A II antagonists:

4'-[(2-butyl-1H-thieno[3,4-d]imidazol-1-yl)methyl]-[1,1'-biphenyl]-2-carboxylic acid;

2-butyl-3-[(2'-carboxy{1,1'-biphenyl}-4-yl)methyl]-3H-thieno[2,3-d]imidazole-5-carboxylic acid methyl ester;

1,4-dihydro-1,3-dimethyl-5-propyl-4-[(2'-{1H-tetrazol-5-yl}{1,1'-biphenyl}-4-yl)methyl]imidazo[4,5-c]-pyrazole;

2-butyl-1-[(2'-{1H-tetrazol-5-yl}{1,1'-biphenyl}-4-yl)methyl]-1H-thieno[2,3-d]imidazole-5-carboxylic acid methyl ester;

Thus, the compounds of the invention are useful in treating hypertension. They are also of value in the management of acute and chronic congestive heart failure, in the treatment of secondary hyperaldosteronism, primary and secondary pulmonary hyperaldosteronism, primary and secondary pulmonary hypertension, renal failure such as diabetic nephropathy, glomerulonephritis; scleroderma and the like, renal vascular hypertension, left ventricular dysfunction, diabetic retinapathy, and in the management of vascular disorders such as migraine or Raynaud's disease. The application of the compounds of this invention for these and similar disorders will be apparent to those skilled in the art.

The compounds of this invention are also useful to treat elevated intraocular pressure and can be administered to patients in need of such treatment with typical pharmaceutical formulation such as tablets, capsules, injectables and the like as well as topical ocular formulations in the form of solutions, ointments, inserts, gels, and the like Pharmaceutical formulations prepared to treat intraocular pressur would typically contain about 0.1% to 15% by weight, prederably 0.5% to 2% by weight, or a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calciu, diflusinal, diltiazem, felodipine, nicardipine, nifedipine, niludipine, nimodipine, nisoldipine, nitrendipine, verapamil, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

DETAILED DESCRIPTION OF THE INVENTION

The following examples are set forth to illustrate preparation of the compounds of the invention and their incorporation into pharmaceutical compositions and as such should not be construed as limiting the invention recited in the appended claims.

EXAMPLE 1

4'-[(2-butyl-1H-thieno[3,4-d]imidazol-1-yl)methyl][1,1'-biphenyl]-2-carboxylic acid (1, A—B—C are =CH—S—CH=; $R^6$=butyl; $R^1$=COOH)

Step A: 2-Butyl-1H-thieno[3,4-d]imidazole

A mixture of 3,4-diaminothiophene (116 mg, 1.01 mmol) and ethyl valeroimidate hydrochloride (504 mg, 3.05 mmol) in absolute ethanol (20 mL) was heated to reflux for 1 hour, cooled to room temperature and stirred for 15 hours. The mixture was concentrated and purified by flash chromatography (SiO$_2$, 25% EtOAc/hexanes) to give 140 mg (78%) of 2-n-butyl-1H-thieno[3,4-d]imidazole as a tan solid: $^1$H NMR (300 MHz, CDCl$_3$)δ 6.70 (s, 2H), 2.81 (t, 2H, J=7.5 Hz), 1.88-1.74 (m, 2H), 1.48-1.35 (m, 2H), 0.90 (t, 3H, J=7.2 Hz); FAB-MS: 181 (M$^+$+1).

Step B:
4'-[(2-butyl-1H-thieno[3,4-d]imidazol-1-yl)-methyl][1,1'-biphenyl]-2-carboxylic acid t-butyl ester To a stirred solution of 2-butyl-1H-thieno-[3,4-d]imidazole (38 mg, 0.211 mmol) in DMF (1.6 mL) at room temperature was added NaH (316 mmol). After 30 minutes, tert-butyl-4'-bromomethylbiphenyl-2-carboxylate (80.5 mg, 0.232 mmol) was added in one portion. The reaction mixture was stirred for 2 hours and brine (5 mL) was added. Extractive workup (EtOAc) and purification by flash chromatography (SiO$_2$, 40% EtOAc/hexane) gave 64 mg (68%) of 4'-[(2-butyl-1H-thieno[3,4-d]imidazol-1-yl)methyl][1,1'-biphenyl]-2-carboxylic acid t-butyl ester as a thick oil: $^1$H NMR (300 MHz, CDCl$_3$) δ 7.78 (dd, 1H, J=7.5 and 1 Hz), 7.48 (td, 1H J=7.5 and 1 Hz), 7.40 (td, 1H, J=7.5 and 1 Hz) 7.32–7.26 (m, 3H), 7.19 (d, 2H, J=8 Hz), 6.99 (d, 1H, J=2.5 Hz), 6.28 (d, 1H, J=2.5 Hz), 5.17 (s, 2H), 2.78 (t, 2H, J=8 Hz), 1.91–1.81 (m, 2H), 1.54–1.41 (m, 2H), 1.23 (s, 9H), 0.96 (t, 3H, J=7 Hz).

Step C:
4'-[(2-butyl-1H-thieno[3,4-d]imidazol-1-yl)methyl][1,1'-biphenyl]-2-carboxylic acid (1, A—B—C are =CH—S—CH=; R$^6$—E=butyl; R$^1$=COOH)

To a solution of the foregoing Step B material (39 mg, 0.087 mmol) in methylene chloride (0.50 mL) at room temperature was added trifluoroacetic acid (0.20 mL). After 18 hours, the solution was evaporated (from benzene) and chromatographed (Sephadex LH-20, MeOH) to give 33 mg (96%) of the title compound as an oil: $^1$H NMR, (300 MHz, CD$_3$OD) δ 7.82 (d, 1H, J=7.5 Hz), 7.55 (t, 1H, J=7.5 Hz), 7.42 (t, 1H, J=7.5 Hz), 7.40–7.34 (m, 5H), 7.32 (d, 1H, J=2 Hz), 6.90 (d, 1H, J=2.5 Hz), 5.49 (s, 2H), 3.13 (t, 2H, J=7.5 Hz), 1.88–1.75 (m, 2H), 1.59–1.43 (m, 2H), 1.00 (t, 3H, J=7 Hz); FAB-MS: m/e 391 (M$^+$+1).

EXAMPLE 2

2-butyl-1-[(2'-{1H-tetrazol-5-yl}{1,1'-biphenyl}-4-yl)methyl]-1H-thieno[3,4-d]imidazole(1, A—B—C are =CH—S—CH=; R$^6$—E=butyl; R$^1$=tetrazol-5-yl)

Step A:
2-butyl-1-[(2'-{N-triphenylmethyltetrazol-5-yl}{1,1'-biphenyl}-4-yl)methyl]-1H-thieno-[3,4-d]imidazole This Step A compound can be prepared in a similar fashion to the preparation of 4'-[(2-butyl-1H-thieno[3,4-d]imidazol-1-yl)methyl][1,1'-biphenyl]-2-carboxylic acid t-butyl ester (Example 1, Step B) except that the alkylating agent used can be 2'-(N-triphenylmethyltetrazol-5-yl)biphen-4-yl methyl bromide in place of t-butyl-4'-bromomethylbiphenyl-2-carboxylate.

Step B:
2-butyl-1-[(2'-{1H-tetrazol-5-yl}{1,1'-bi-phenyl}-4-yl)methyl]-1H-thieno[3,4-d]-imidazole This Step B material can be prepared by deblocking the Step A material with aqueous HOAc at 50° C. as described for a related procedure (see Example 11, Step F below) to give the title compound.

EXAMPLE 3

2-butyl-3-[(2'-carboxy{1,1'-biphenyl}-4-yl)methyl]-3H-thieno[2,3-d]imidazole-5-carboxylic acid methyl ester (1, A—B—C are —CH=C(CO$_2$CH$_3$)—S—; R$^6$=butyl; R$^1$=COOH)

Step A:
2-Butyl-1-[(2'-t-butoxycarbonylbiphen-4-yl)-methyl]-5-chloro-1H-imidazole-4-carboxaldehyde A mixture of 2-butyl-1-[(2'-t-butoxycarbonylbiphen-4-yl)methyl]-5-chloro-1H-imidazole-4-methanol (European Patent Applications 253,310) (145 mg, 319 mmol), MnO$_2$ (550 mg, 6.4 mmol), 3A powdered sieves (500 mg) in CH$_2$Cl$_2$ (10 mL) was stirred at room temperature for 3 hours. The mixture was filtered and evaporated to give 142 mg of the title compound as a glass. $^1$H NMR (300 MHz, CD$_3$OD)δ 9.82 (s, 1H), 7.70 (dd, 1H, J=7 and 1.5 Hz), 7.50 (td, 1H, J=7 and 1.5 Hz), 7.40 (td, 1H, J=7 and 1.5 Hz), 7.31–7.26 (m, 3H), 7.15 (apparent d, 2H, J=3 Hz), 5.38 (s, 2H), 2.73 (t, 2H, J=7.5 Hz), 1.72–1.62 (m, 2H), 1.45–1.30 (m, 2H) 1.21 (s, 9H), 0.90 (t, 3H, J=7 Hz).

Step B:
2-butyl-3-[(2'-t-butoxycarbonyl{1,1'-bi-phenyl}-4-yl)methyl-3H-thieno[2,3-d]-imidazole-5-carboxylic acid methyl ester A mixture of the aldehyde described in Step A (25 mg, 55 μmol), methyl thioglycolate (15 μmL, 166 μmol), NaOMe (9 mg, 166 μmol) in dry MeOH (1 mL) was heated to reflux for 2 hours. The mixture was cooled, 1 drop of 30% H$_2$O$_2$ was added, then after 5 minutes 5 mg of sodium bisulfite in 0.5 mL of H$_2$O was added. Evaporation and purification by chromatography (SiO$_2$, 25% EtOAc/hexanes) gave 4 mg of the title compound as an oil.

$^1$H NMR (300 MHz, CDCl$_3$)δ 7.84 (s, 1H), 7.79 (dd, 1H, J=8 and 1.5 Hz), 7.49 (td, 1H, J=7 and 1.5 Hz), 7.41 (td, 1H, J=7 and 1.5 Hz) 7.36–7.20 (m, 5H), 5.25 (s, 2H), 3.88 (s, 3H), 2.91 (t, 2H, J=7.5 Hz), 1.93–1.81 (m, 2H), 1.56–1.40 (m, 2H), 1.27 (s, 9H), 0.98 (t, 3H, J=7.5 Hz). FAB-MS: m/e 505 (M$^+$+1).

Step C:
2-butyl-3-[(2'-carboxy{1,1'-biphenyl}-4-yl)-methyl]-3H-thieno[2,3-d]imidazole-5-carboxylic acid methyl ester A mixture of 3.5 mg of the foregoing Step B material in 2 mL of 1:1 trifluoroacetic acid/CH$_2$Cl$_2$ was stirred at room temperature for 16 hours. Evaporation and chromatography (SiO$_2$, 10% MeOH/CH$_2$Cl$_2$) gave 3.2 mg of the title compound as an oil: $^1$H NMR (300 MHz, 4:1 CDCl$_3$/CD$_3$OD)δ 7.81 (dd, 1H, J=7.5 and 1.5 Hz), 7.73 (s, 1H), 7.48 (td, 1H, J=7.5 and 1.5 Hz), 7.37 (td, 1H, J=7.5 and 1.5 Hz), 7.36 (d, 2H, J=8 Hz), 7.29 (dd, 1H, J=7.5 and 1.5 Hz), 7.21 (d, 2H, J=8 Hz), 5.21 (s, 2H), 3.82 (s, 3H), 2.88 (t, 2H, J=7 Hz), 1.83–1.72 (m, 2H), 1.50–1.37 (m, 2H), 0.95 (t, 3H, J=7 Hz). FAB-MS: m/e 449 (M$^+$+1).

EXAMPLE 4

2-butyl-1-[(2'-carboxy{1,1'-biphenyl}-4-yl)methyl]-1H-thieno[2,3-d]imidazole-5-carboxylic acid methyl ester (1, A—B—C are —S—C(CO$_2$CH$_3$)=CH—; R$^6$—E=butyl; R$^1$=COOH)

Step A:
2-Butyl-1-[(2'-t-butoxycarbonylbiphen-4-yl)-methyl]-4-chloro-1H-imidazole-5-carboxaldehyde This Step A compound was prepared as described in Example 3, Step A starting with 2-butyl-1-[(2'-t-butoxycarbonylbiphen-4-yl)methyl]-4-chloro-1H-imidazole-5-methanol. $^1$H NMR (250 MHz, CDCl$_3$)δ 9.78 (, 1H), 7.78 (dd, J=7 and 1 Hz), 7.52–7.35 (m, 2H), 7.32–7.35 (m, 3H), 7.08 (d, 2H), J=8 Hz), 5.60 (s, 2H), 2.70 (t, 2H, J=7.5 Hz) 1.82–1.30 (m, 2H), 1.49–1.35 (m, 2H), 1.23 (s, 9H) 0.95 (t, 3H, J=7.5 Hz).

Step B:
2-butyl-1-[(2'-t-butoxycarbonyl{1,1'-bi-phenyl}-4-yl)methyl]-1H-thieno[2,3-d]-imidazole-5-carboxylic acid methyl ester This Step B compound was prepared as described in Example 3, Step B starting from the chloro aldehyde prepared in Example 4, Step A, with the exception that the reaction was refluxed for 24 hours. FAB-MS: m/e 504 (M+).

Step C:
2-butyl-1-[(2'-carboxy{1,1'-biphenyl}-4-yl)-methyl]-1H-thieno[2,3-d]imidazole-5-carboxylic acid methyl ester The title compound can be prepared by deblocking the foregoing Step B material with trifluoroacetic acid/$CH_2Cl_2$ (1:1) as described above in Example 3, Step C.

EXAMPLE 5

2-butyl-3-[(2'-{1H-tetrazol-5-yl}{1,1'-biphenyl}-4-yl)methyl]-3H-thieno[2,3-d]imidazole-5-carboxylic acid methyl ester (1, A—B—C are —CH=C($CO_2CH_3$)—S—; $R^6$—E=n-butyl; $R^1$=tetrazol-5-yl)

Step A:
2-Butyl-1-[(2'-{N-triphenylmethyltetrazol-5-yl}biphen-4-yl)methyl]-5-chloro-1H-imidazole-4-carboxaldehyde This Step A compound can be prepared as described in Example 3, Step A, except that 2-butyl-1-[(2'-{N-triphenylmethyltetrazol-5-yl}biphen-4-yl)-methyl]-5-chloro-1H-imidazole-4-methanol (European Patent Applications 253,310 and 291,969) can be used as the starting material for the oxidation instead of 2-butyl-1-[(2'-t-butoxycarbonylbiphen-4-yl)methyl]-5-chloro-1H-imidazole-4-methanol.

Step B:
2-Butyl-1-[(2'-{N-triphenylmethyltetrazol-5-yl}{1,1'-biphenyl}-4-yl)methyl]-4-methoxycarbonylmethylthio-1H-imidazole-4-carboxyaldehyde A mixture of the aldehyde prepared as described in Example 5, Step A (100 mg, 164 mmol), methyl thioglycolate (15 μL, 166 μmol), NaH (6.4 mg of an 80% dispersion, 213 μmol) in dry THF was stirred at room temperature for 20 minutes. Concentration and purification by chromatography ($SiO_2$, 50% EtOAc/hexanes) gave 56 mg of the title compound as an oil. $^1$H NMR (300 MHz, $CDCl_3$) δ 7.92 (dd, J=7 and 1.5 Hz), 7.53–7.42 (m, 2H), 7.38–7.22 (m, 10H), 7.12 (d, 2H, J=8 Hz), 6.98–6.92 (m, 6H), 6.76 (d, 2H, J=8 Hz) 5.29 (s, 2H), 3.61 (s, 3H), 3.50 (s, 2H) 2.56 (t, 2H, J=8 Hz) 1.75–1.62 (m, 2H), 1.34–1.22 (m, 2H), 0.85 (t, 3H, J=7 Hz).

Step C:
2-Butyl-3-[(2'-{1H-tetrazol-5-yl}{1,1'-bi-phenyl}-4-yl)methyl]-3H-thieno[2,3-d]-imidazole-5-carboxylic acid methyl ester A solution of 31 mg of the foregoing Step B compound and NaOMe (9.2 mg) in MeOH (1 mL) was heated to reflux for 15 minutes. Acetic acid (1 mL) was added, and the mixture was heated to reflux for 1 hour, evaporated to dryness, and purified by chromatography ($SiO_2$, 80:20:1 $CH_2Cl_2$/MeOH/$NH_4OH$) to give 10 mg of the title compound as a white solid. $^1$H NMR (300 MHz, $CDCl_3$)δ 7.76 (s, 1H) 7.72–7.60 (m, 4H) 7.19 (apparent q, 4H, J=7.5 Hz), 5.33 (s, 2H), 3.87 (s, 3H), 2.93 (t, 2H, J=8 Hz), 1.83–1.70 (m, 2H), 1.52–1.40 (m, 2H), 0.97 (t, 3H, J=7 Hz).

EXAMPLE 6

2-butyl-1-[(2'-{1H-tetrazol-5-yl}{1,1'-biphenyl}-4-yl)methyl]-1H-thieno[2,3-d]imidazole-5-carboxylic acid methyl ester (1, A—B—C are —S—C($CO_2CH_3$)=CH—; $R^6$—E=n-butyl; $R^1$=tetrazol-5-yl)

Step A:
2-Butyl-1-[(2'-{N-triphenylmethyltetrazol-5-yl}{1,1'-biphenyl}-4-yl)methyl]-4-chloro-1H-imidazole-5-carboxaldehyde This Step A compound can be prepared as described in Example 3, Step A except that 2-butyl-1-[(2'-N-triphenylmethyltetrazol-5-yl}{1,1'-biphenyl}-4-yl)methyl]-4-chloro-1H-imidazole-5-methanol can be used as the starting material for the oxidation instead of 2-butyl-1-[(2'-t-butoxycarbonylbiphen-4-yl)methyl]-5-chloro-1H-imidazole-4-methanol.

Step B:
2-Butyl-1-[(2'-{N-{triphenylmethyltetrazol-5-yl}{1,1'-biphenyl}-4-yl)methyl]-4-methoxycarbonylmethylthio-1H-imidazole-5-carboxyaldehyde The foregoing Step A material can be treated with methyl thioglycolate in the presence of base in a fashion similar to that described for Example 5, Step B, to give the title compound.

Step C:
2-Butyl-1-[(2'-{1H-tetrazol-5-yl}{1,1'-bi-phenyl}-4-yl)methyl]-1H-thieno[2,3-d]-imidazole-5-carboxylic acid methyl ester The foregoing Step B material can be treated in the same manner as described in Example 5, Step C to give the title compound.

EXAMPLE 7

2-butyl-3-[(2'-{1H-tetrazol-5-yl}{1,1'-biphenyl}-4-yl)methyl]-3H-thieno[2,3-d]imidazole-5-carboxylic acid (1, A—B—C are —CH=C($CO_2H$)—S—; $R^6$—E=butyl; $R^1$=tetrazol-5-yl)

2-butyl-3-[(2'-{1H-tetrazol-5-yl}{1,1'-bi-phenyl}-4-yl)methyl]-3H-thieno[2,3-d]-imidazole-5-carboxylic acid methyl ester (1, A—B—C are —CH=C($CO_2CH_3$)—S—; $R^6$—E=butyl; $R^1$=tetrazol-5-yl) prepared as described in Example 5 can be saponified with lithium hydroxide hydrate in THF/$H_2O$ (5:1) at room temperature for 24 hours to give the title compound.

EXAMPLE 8

2-butyl-3-[(2'-carboxyl{1,1'-biphenyl}-4-yl)methyl]-3H-thieno[2,3-d]imidazole-5-carboxylic acid (1, A—B—C are —CH=C($CO_2H$)—S—; $R^6$—E=butyl; $R^1$=$CO_2H$ The title compound can be prepared as described in Example 7 except that 2-butyl-3-[(2'-carboxy{1,1'-biphenyl}-4-yl)methyl]-3H-thieno[2,3-d]-imidazole-5-carboxylic acid methyl ester (1, A—B—C are CH=C($CO_2CH_3$)—S—; $R^6$—E=n-butyl; $R^1$=$CO_2H$) prepared as described in Example 3 can be used as the starting material for the saponification.

EXAMPLE 9

2-butyl-1-[(2'-carboxy{1,1'-biphenyl}-4-yl)methyl]-1H-thieno[2,3-d]imidazole-5-carboxylic acid (1, A—B—C are S—C(CO$_2$CH$_3$)=CH—; R$^6$—E=butyl; R$^1$=CO$_2$H)

The title compound can be prepared as described in Example 7 except that 2-butyl-1-[(2'-carboxy{1,1'-biphenyl}-4-yl)methyl]-1H-thieno[2,3-d]-imidazole-5-carboxylic acid methyl ester (1, A—B—C are —S—C(CO$_2$CH$_3$)=CH—; R$^6$—E=butyl; R$^1$=CO$_2$H) prepared as described in Example 4 can be used as the starting material for the saponification.

EXAMPLE 10

2-butyl-1-[(2'-{1H-tetrazol-5-yl}{1,1'-biphenyl}-4-yl)methyl]-1H-thieno[2,3-d]imidazole-5-carboxylic acid (1, A—B—C are S—C(CO$_2$H)=CH—; R$^6$—E—butyl; R$^1$=tetrazol-5-yl)

The title compound can be prepared as described in Example 7 except that 2-butyl-1-[(2'-{1H-tetrazol-5-yl}{1,1'-biphenyl}-4yl)methyl]-1H-thieno-[2,3-d]imidazole-5-carboxylic acid methyl ester (1, A—B—C are —S—C(CO$_2$CH$_3$)=CH—; R$^6$—E=butyl; R$^1$=tetrazol-5-yl) prepared as described in Example 6 can be used as the starting material for the saponification.

EXAMPLE 11

1,4-Dihydro-1,3-dimethyl-5-propyl-4-[(2'{1H-tetrazol-5-yl}{1,1'-biphenyl}-4-yl)methyl]imidazo[4,5-c]-pyrazole (1, A—B—C are —N(CH$_3$)—N=C(CH$_3$)—; R$^6$—E=butyl; R$^1$=tetrazol-5-yl)

Step A: 5-Butyramido-1,3-dimethylpyrazole

A stirred solution under nitrogen of 5-amino-1,3-dimethylpyrazole (7.09 g, 63.8 mmol) and triethylamine (10 mL) in sieve-dried methylene chloride (100 mL) was chilled in an ice-bath and n-butyryl chloride (7.3 mL, 70.3 mmol) was added dropwise. After 1 hour, the reaction mixture was shaken with 50 mL of 1M K$_2$HPO$_4$ solution and the aqueous phase was further extracted with CH$_2$Cl$_2$ (2×70 mL). The organic phase was dried over MgSO$_4$, filtered and then evaporated to dryness to give 13.2 g of an orange-yellow oil. This was purified by chromatography on SiO$_2$ (300 g), developing with EtOAc/hexane (45:55) to give the Step A compound (10.53 g; 91%) as an oil. $^1$H NMR (200 MHz, CDCl$_3$), δ 6.00 (s, 1H), 3.65 (s, 3H), 2.37 (t, 2H, J=9 Hz), 2.22 (s, 3H), 1.62-1.90 (m, 2H), 1.01 (t, 3H, J=9 Hz).

Step B: 5-Butylamino-1,3-dimethylpyrazole

To a stirred solution of 5-butyramido-1,3-dimethyl-pyrazole (9.60 g, 53 mmol) in dry THF (80 mL) there was added dropwise over a period of 5 minutes, under nitrogen, a 1M solution of LiAlH$_4$ in THF (68.4 mL). The mixture was then stirred under nitrogen for 3 hours at 65° C. (oil bath temperature) and then at room temperature for 18 hours. This solution was chilled and well stirred while H$_2$O (approx. 20 mL) was carefully added. After 15 minutes the suspension was filtered and the solid was washed on the pad with EtOAc. The organic phase in the filtrate was separated, dried over MgSO$_4$ and evaporated to dryness to give 8.6 g of amide product which was purified by chromatography on a SiO$_2$ column (200 g) developed with EtOAc/hexanes (40:60) to give the Step B compound (7.9 g, 89%) as an oil.

$^1$H NMR (200 MHz, CDCl$_3$)δ 5.27 (s, 1H), 3.53 (s, 3H), 3.06 (d of t, 2H), 2.17 (s, 3H), 1.52-1.66 (m, 2H), 1.31-1.49 (m, 2H), 0.95 (t, 3H, J=9 Hz).

Step C: 5-Butylamino-4-nitroso-1,3-dimethylpyrazole

To a stirred solution of 5-butylamino-1,3-dimethylpyrazole (4.0 g, 23.9 mmol) in EtOH (100 mL) there was added dropwise, under nitrogen, isoamyl nitrite (35 mL) and the mixture was stirred at room temperature for 3 hours. The progress of the reaction was monitored by tlc (SiO$_2$, developed with EtOAc/hexanes [3:2]) and when no starting material remained, the solution was evaporated to dryness. This mixture was purified by chromatography on a SiO$_2$ column (400 mL) developed with EtOAc/hexanes (40:60). The faster components were eluted first (one of which is the isomeric N-nitroso derivative which can be isomerized with acid to yield additional product) followed by the Step C compound (3.23 g, 69%) as reddish crystals.

$^1$H NMR (200 MHz, CDCl$_3$)δ 3.77 (s, 3H), 3.47 (d of t, 2H), 2.61 (s, 3H), 1.53-1.70 (m, 2H), 1.37-1.52 (m, 2H), 0.96 (t, 3H, J=9 Hz). M.p 49°-101° C. Anal.

Calcd for C$_4$H$_{16}$N$_4$O; C, 55.08; H, 8.22; N, 28.55; Found: C, 55.11; H, 8.16; N, 28.23.

Step D: 1,4-Dihydro-1,3-dimethyl-5-propylimidazo-[4,5-c]pyrazole

The foregoing Step C material (156.6 mg, 0.80 mmol) was dissolved in pyridine (2 mL) and heated under nitrogen, under a reflux condenser at 110° C. for 5 hours. The reaction was monitored by tlc (SiO$_2$, developed with CHCl$_3$/MeOH/NH$_4$OH [90:9:1]) until complete when the mixture was cooled and evaporated to dryness. This crude product was purified by preparative tlc on 1000μ SiO$_2$ plates developed with CHCl$_3$/MeOH/NH$_4$OH [90:9:1]) until complete when the mixture was cooled and evaporated to dryness. This crude product was purified by preparative tlc on 1000μ SiO$_2$ plates developed with CHCl$_3$/MeOH/NH$_4$OH (90:9:1) to give the Step D compound (104 mg, 73%) as a dark oil.

$^1$H NMR (200 MHz, CDCl$_3$)δ 3.88 (s, 3H), 2.79 (t, 2H, J=9 Hz), 2.34 (s, 3H), 1.72-1.91 (m, 2H), 1.00 (t, 3H).

Step E: 1,4-Dihydro-1,3-dimethyl-5-propyl-4-[(2'-{N-triphenylmethyltetrazol-5-yl}{1,1'-biphenyl}-4-yl)methyl]imidazo[4,5-c]pyrazole The foregoing Step D material (49.5 mg, 0.28 mmol) was dissolved in sieve dried DMF (0.5 mL) and 60% NaH in mineral oil (35.1 mg, 0.53 mmol of NaH) was added. After the evolution of hydrogen was complete, the suspension was centrifuged and the clear supernatant was removed and treated with a solution of 2'-(N-triphenylmethyltetrazol-5-yl)-biphen-4-yl-methyl bromide (259.1 mg, 0.46 mmol) in dry DMF (1 mL). After stirring overnight at room temperature under nitrogen, a second portion of 60% NaH in oil (25 mg, 0.38 mmol of NaH) was added and the mixture was heated at 50° C. for 4.5 hours. The DMF was removed by evaporation under reduced pressure and the residue was partitioned between CHCl$_3$ and 1M KH$_2$PO$_4$. The organic phase was evaporated to dryness and the Step E compound was purified by preparative tlc on 1000μ SiO$_2$ plates developed with CHCl₃/MeOH/NH₄OH (95:5:05) to give 65 mg (35%) of the pure product.

¹H NMR (200 MHz, CDCl₃) δ 7.87-7.94 (m), 6.84-7.53 (m), 5.09 (s), 3.90 (s), 2.66 (t, J=9 Hz), 2.03 (s), 1.65-1.85 (m), 0.96 (t, J=9 Hz).

Step F:
1,4-Dihydro-1,3-dimethyl-5-propyl-4-[(2'-{1H-tetrazol-5-yl}{1,1'-biphenyl}-4-yl)methyl]-imidazo[4,5-c]pyrazole The material prepared in Step E (160 mg, 0.24 mmol) was dissolved in glacial HOAc (2.0 mL) at 50° C. and H₂O was added dropwise until the solution just became cloudy (approx. 0.7 mL). The mixture was kept at 50° C. for 2 hours and then was evaporated to dryness under a stream of nitrogen. The residue so formed was purified by preparative tlc on 1000μ SiO₂ plates developed with CHCl₃/MeOH/NH₄OH (80:20:2) to give 67 mg (68%) of the title compound as its ammonium salt.

¹H NMR (200 MHz, DMSO-d₆) δ 6.82-7.80 (m), 5.21 (s), 3.66 (s), 2.70 (t, J=9 Hz), 1.93 (s), 1.52-1.76 (m), 0.89 (t, J=9 Hz). FAB-MS: 413 (M⁺+1).

Anal. Calcd for C₂₃H₂₄N₈·NH₃·0.6 H₂O; C, 62.74; H, 6.46; N, 28.63; Found: C, 62.49; H, 6.24; N, 28.73.

EXAMPLE 12

1,4-Dihydro-1,2-dimethyl-5-propyl-4-[(2'-{1H-tetrazol-5-yl}{1,1'-biphenyl}-4-yl)methyl]imidazo[4,5-d]-imidazole; (1, A—B—C are —N(CH₃)—C(CH₃)=N—; R⁶—E=propyl; R¹=tetrazol-5-yl) and
1,6-dihydro-1,2-dimethyl-5-propyl-6-[(2'-{1H-tetrazol-5-yl}{1,1'-biphenyl}-4-yl)methyl]imidazo[4,5-d]imidazole; (1, A—B—C are —N=C(CH₃)—N(CH₃)—; R⁶—E=propyl; R¹=tetrazol-5-yl)

Step A: 5-Amino-1,2-dimethylimidazole

To a stirred solution of K₂CO₃ (6.9 g, 50 mmol) in H₂O (20 mL) and Et₂O (10 mL) was carefully added aminoacetonitrile bisulfate (7.7 g, 50 mmol). When the reaction had subsided, additional Et₂O (100 mL) was added and the mixture was vigorously stirred for 10 minutes. The organic layer was decanted, additional Et₂O (100 mL) was added to the reaction mixture which was again stirred vigorously for 10 minutes. After decantation of the Et₂O layers, this procedure was repeated 5 times and the pooled Et₂O layers were dried over MgSO₄, filtered and concentrated under a nitrogen stream to approximately 25 mL, at which point it was again dried, filtered and concentrated to a yellowish oil (1.5 g). ¹H NMR (200 MHz, CDCl₃) δ 4.09 (s, 2H), 4.07 (q, 2H, J=9 Hz), 1.95 (s, 3H), 1.25 (t, 3H, J=9 Hz). This material was somewhat unstable and was immediately combined with mixture of abs. EtOH (5 mL) and methylamine (the EtOH was previously chilled to 0° C. and gaseous methylamine was bubbled into the solution until the final volume approached 10 mL, approximately 5 g of methylamine), stoppered tightly and allowed to stand at ambient temperature for 90 hours. The reaction mixture was then concentrated under a nitrogen stream to give the title compound as plate-like off-white crystals, after filtration and washing with a little abs. EtOH followed by Et₂O. Yield 0.98 g (17.76% overall) after reworking the mother liquors. mp 150°-155° (dec); ¹H NMR, (200 MHz, CDCl₃) δ 6.39 (s, 1H), 3.39 (s, 3H), 2.31 (s, 3H); FAB-MS: m/e 112 (M⁺+1).

Anal. Calcd for C₅H₉N₃ (4% inorganic ash); C, 51.87; H, 7.83; N, 36.30; Found: C, 52.14; H, 7.76; N, 36.30.

Step B: 5-Butyramido-1,2-dimethylimidazole

To a suspension of the foregoing Step A material (545 mg, 4.9 mmol) in dry THF (10 mL) was added butyric anhydride (1.0 mL, 6.1 mmol) and Et₃N (1.0 mL, 7.2 mmol), with stirring under a nitrogen atmosphere. After 18 hours a deep yellow clear solution was obtained and 0.5M K₂HPO₄ (40 mL) was added. This mixture was extracted with CHCl₃ (4×20 mL) and the organic layers were pooled, dried over MgSO₄, filtered and concentrated to a brown gum under a nitrogen stream. This crude product was purified by preparative tlc on eight 8"×8"×1000μ GF silica plates developed with CHCl₃:MeOH:conc NH₄OH (90:10:1). The title compound (lower R_f of two major bands) was eluted using CHCl₃:MeOH:conc. NH₄OH (70:30:3) and evaporation to dryness gave an orange-colored gum. Yield 351 mg (40%); ¹H NMR, (200 MHz, CDCl₃) δ 6.73 (s, 1H), 3.35 (s, 3H), 2.39 (t, 2H, J=9 Hz), 2.34 (s, 3H), 1.66-1.84 (m, 2H), 1.02 (t, 3H, J=9 Hz); FAB-MS: m/e 182 (M⁺+1).

Step C: 5-Butylamino-1,2-dimethylimidazole

To a vigorously stirred solution of the foregoing Step B material (340 mg, 1.9 mmol) in dry THF (5 mL) under nitrogen was added carefully, 1M LiAlH₄ in THF (2.0 mL). The clear solution became cloudy as the addition proceeded. When the addition was complete, the suspension was stirred for 10 minutes at room temperature and then was heated at 65° C. (oil-bath temp.) for 3.5 hours, before being allowed to stand at ambient temperature for an additional 10 hours. To the dark-colored, vigorously stirred mixture was carefully added EtOAc (1-2 mL) followed by H₂O (approximately 0.5 mL) and the suspension was well-stirred for 15 minutes. Solid MgSO₄ was added, the mixture was filtered and the filtrate was evaporated to dryness under a nitrogen stream to give a soft solid. After dissolution in Et₂O and concentration to an oil, crystallization occurred. ¹H NMR (200 MHz, CDCl₃) δ 7.26 (s, 1H), 2.62 (s, 3H), 2.97 (d of t, 2H) 2.30 (s, 3H), 1.51-1.66 (m, 2H), 1.31-1.49 (m, 2H).

Step D: 5-Butylamino-1,2-dimethyl-4-nitrosoimidazole

To a solution of the foregoing Step C material (275 mg, 1.65 mmol) in abs. EtOH (4 mL) was added dropwise, with stirring, isoamyl nitrite (1.0 mL, 0.87 g, 8.6 mmol). After stirring for 24 hours the reaction mixture was concentrated to an oil under a stream of nitrogen and the crude product was purified by preparative tlc on three 8"×8"×1000μ GF silica gel plates developed with CHCl₃:MeOH:conc. NH₄OH (90:10:1). The title compound was isolated (118 mg) as a reddish solid which was further purified by rinsing with a minimum volume of CHCl₃ to give a colorless solid. ¹H NMR (200 MHz, CDCl₃) δ 8.3-9.0 (br s), 3.79 (t, 2H, J=9 Hz), 3.19 (s, 3H), 2.32 (s, 3H), 1.55-1.74 (m, 2H), 1.33-1.55 (m, 2H), 0.93 (t, 3H, J=10 Hz); FAB-MS: m/e 197 (M⁺+1).

Anal. Calcd for C₉H₁₆N₄O; C, 55.08; H, 8.22; N, 28.55; Found: C, 55.10; H, 8.08; N, 28.55.

Step E:
1,4-Dihydro-1,2-dimethyl-5-propylimidazo[4,5-d]imidazole

A solution of the foregoing Step D material (10 mg) in sieve-dried DMF (0.5 mL) was heated under nitrogen at 130° C. for 4 hours. The solution was then concentrated to dryness under a stream of nitrogen and the residue was applied to a preparative 8"×8"×1000μ GF silica gel tlc plate which was developed with CHCl$_3$:MeOH:conc. NH$_4$OH (90:10:1). The band of product was eluted and evaporated to an orange gum (5 mg) which could be crystallized from EtOAc or acetone. $^1$H NMR, (200 MHz, CDCl$_3$) δ 3.72 (s, 3H), 2.84 (t, 2H, J=9 Hz), 2.52 (s, 3H), 1.74–1.93 (m, 2H), 0.95 (t, 3H, J=9 Hz); FAB-MS: m/e 179 (M$^+$+1).

Anal. Calcd for C$_9$H$_{14}$N$_4$.0.1 H$_2$O; C, 60.04; H, 7.95; N, 31.12; Found: C, 60.03; H, 7.69; N, 30.77.

Step F:
1,4-Dihydro-1,2-dimethyl-5-propyl-4-[(2'-{N-triphenylmethyltetrazol-5-yl}{1,1'-biphenyl}-4-yl)methyl]imidazo[4,5-d]imidazole; and
1,6-dihydro-1,2-dimethyl-5-propyl-6-[(2'-{N-triphenylmethyltetrazol-5-yl}{1,1'-biphenyl}-4-yl)methyl]imidazo[4,5-d]imidazole The foregoing Step E material can be alkylated in a similar fashion to that described in Example 11 Step E using NaH in DMF and 2'-(N-triphenylmethyltetrazol-5-yl)biphen-4-yl-methyl bromide to give the regioisomeric title compounds which can be separated by chromatographic methods and identified by NMR methods.

Step G:
1,4-Dihydro-1,2-dimethyl-5-propyl-4-[(2'-{H-tetrazol-5-yl}{1,1'-biphenyl}-4-yl)methyl]-imidazo[4,5-d]imidazole To a solution of 42 mg of the foregoing Step F material in 4.0 ml glacial acetic acid was added 200×H$_2$O with stirring while heating ina 60° C. oil bath. The slightly cloudy solution became clear in 10 min., after which another 50× of H$_2$O was added. A suspension resulted which was stirred an heated at 60° C. for 1.5 hours. After cooling and centrifugution, the supernatent phase was evaporated to dryness with N$_2$ and the residue chromatographed on a single 8"×8"×1000μ silica gel GF plate useing 2:20:80 conc. NH$_4$OH:MeOH:CHCl$_3$. The product exhibited a $^1$H NMR (200 MHz, CDCl$_3$)δ 7.8–7.7, 7.6–7.3, 7.2–6.7 (m; aromatic protons), 5.06 (s; N.CH$_2$.Ar), 3.63 (S; CH$_3$.N), 2.69 (t, J=4 Hz; Im.CH$_2$.c), 2.37 (S; CH$_3$.Im), 1.8–1.6 (m, J=4 Hz; C.CH$_2$.C), 0.94 (t, J=4 Hz; C-CH$_3$); FAB-MS:m/e 413 (M$^+$+1).

Step H:
1,6-Dihydro-1,2-dimethyl-5-propyl-6-[(2'-{1H-tetrazol-5-yl}{1,1'-biphenyl}-4-yl)methyl]imidazo[4,5-d]-imidazole 1,6-Dihydro-1,2-dimethyl-5-propyl-6-[(2'-{N-triphenylmethyltetrazol-5-yl}{1,1'-biphenyl}-4-yl)methyl]imidazo[4,5-d]imidazole prepared as described above in Step F can be deblocked with aqueous HOAc at 50° C. as described for a related procedure (see Example 11, Step F) to give the title compound.

EXAMPLE 13

4'-[1,4-Dihydro-1,2-dimethyl-5-propylimidazo[4,5-d]imidazol-4-yl)methyl][1,1'-biphenyl]-2-carboxylic acid (1, A—B—C are —N(CH$_3$)—C(CH$_3$)=N—; R$^6$—E=propyl; R$^1$=COOH) and
4'-[1,6-dihydro-1,2-dimethyl-5-propylimidazo[4,5-d]imidazol-6-yl)methyl][1,1'-biphenyl]-2-carboxylic acid (1, A—B—C are —N=C(CH$_3$)—N(CH$_3$)—; R$^6$—E=propyl; R$^1$=COOH)

Step A:
4'-[(1,4-Dihydro-1,2-dimethyl-5-propylimidazo[4,5-d]imidazol-4-yl)methyl][1,1'-biphenyl]-2-carboxylic acid t-butyl ester and
4'-[(1,6-dihydro-1,2-dimethyl-5-propylimidazo[4,5-d]imidazo-6-yl)methyl[]1,1'-biphenyl]-2-carboxylic acid t-butyl ester;

1,4-Dihydro-1,2-dimethyl-5-propylimidazo [4,5-d]imidazole (as prepared in Example 12, Step E) can be alkylated in a similar fashion to that described in Example 1, Step B using NaH in DMF and t-butyl-4'-bromomethylbiphenyl-2-carboxylate to give the regiosomeric title compounds which can be separated by chromatographic methods and identified by NMR methods.

Step B: 4'-[1,4-Dihydro-1,2-dimethyl-5-propylimidazo [4,5-d]imidazol-4-yl)methyl][1,1'-biphenyl]-2-carboxylic acid The title compound can be prepared by deblocking the 4'-[(1,4-dihydro-1,2-dimethyl-5-propylimidazo[4,5-d]imidazol-4-yl)methyl][1,1'-biphenyl]-2-carboxylic acid t-butyl ester, prepared as described above in Step A, with trifluoroacetic acid /CH$_2$Cl$_2$ (1:1) as described in Example 3, Step C.

Step C: 4'-[1,6-Dihydro-1,2-dimethyl-5-propylimidazo [4,5-d]imidazol-6-yl)methyl][1,1'-biphenyl]-2-carboxylic acid The title compound can be prepared by deblocking the 4'-[(1,6-dihydro-1,2-dimethyl-5-propylimidazo[4,5-d]imidazol-6-yl)methyl[]1,1'-biphenyl]-2-carboxylic acid t-butyl ester, prepared as descrobed above in Step A, with trifluoroacetic acid/CH$_2$Cl$_2$ (1:1) as described in Example 3, Step C.

EXAMPLE 14

Typical Pharmaceutical Compositions Containing a Compound of the Invention

| A: Dry Filled Capsules Containing 50 mg of Active Ingredient Per Capsule | |
|---|---|
| Ingredient | Amount per capsule (mg) |
| 4'-[(2-butyl-1H-thieno[3,4-d]imidazol-1-yl)methyl][1,1'-biphenyl]-2-carboxylic acid | 50 |
| Lactose | 149 |
| Magnesium stearate | 1 |
| Capsule (size No. 1) | 200 |

The 4'-[(2-butyl-1H-thieno[3,4-d]imidazol-1-yl)methyl][1,1'-biphenyl]-2-carboxylic acid can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 4'-[(2-butyl-1H-thieno[3,4-d]imidazol-1-yl)methyl][1,1'-biphenyl]-2-carboxylic acid (25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of 4'-[(2-butyl-1H-thieno[3,4-d]imidazol-1-yl)methyl][1,1'-biphenyl]-2-carboxylic acid (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 4'-[(2-butyl-1H-thieno [3,4-d]imidazol-1-yl)methyl][1,1'-biphenyl]-2-carboxylic acid (1-25 mg), butylated hydroxyanisol (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectible formulation would contain 4'-[(2-butyl-1H-thieno[3,4-d]imidazol-1-yl)methyl][1,1'-biphenyl]-2-carboxylic acid (5.42 mg), sodium phosphate dibasic anhydrous (11.4 mg) benzylalcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound having the formula:

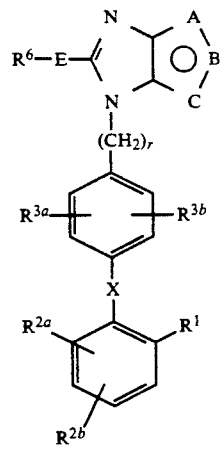

or a pharmaceutically acceptable salt thereof wherein:
$R^1$ is
 (a) —COOH,
 (b) —SO$_2$NH-heteroaryl as defined below,
 (c) —CH$_2$SO$_2$NH-heteroaryl as defined below,
 (d) —SO$_2$NH—CO—$R^{21}$,
 (e) —CH$_2$SO$_2$NH—CO—$R^{21}$,
 (f) —CONH—SO$_2$R$^{21}$,
 (g) —CH$_2$CONH—SO$_2$R$^{21}$,
 (h) —NHSO$_2$NHCO—$R^{21}$,
 (i) —NHCONHSO$_2$R$^{21}$,
 (j) —SO$_2$NHCONHR$^{21}$, (k) 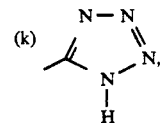

wherein:
heteroaryl is an unsubstituted, monosubstituted or disubstituted five-membered aromatic ring which can contain from 1 to 3 nitrogen atoms and wherein the substituents are members selected from the group consisting of —OH, —SH, —C$_1$-C$_4$-alkyl, —C$_1$-C$_4$-alkoxy, —CF$_3$, halo(Cl, Br, F, I), —NO$_2$, —CO$_2$H, —CO$_2$-C$_1$-C$_4$-alkyl, —NH$_2$, NH(C$_1$-C$_4$-alkyl) and —N(C$_1$-C$_4$-alkyl)$_2$;
$R^{2a}$ is H;
$R^{2b}$ is H, Cl, C$_1$-C$_4$-alkyl, or C$_1$-C$_4$-alkoxy;
$R^{3a}$ is H,
$R^{3b}$ is
 (a) H,
 (b) Cl,
 (c) C$_1$-C$_4$-alkyl,
 (d) C$_5$-C$_6$-cycloalkyl, or
 (e) C$_1$-C$_4$-alkoxy;
wherein aryl is phenyl or naphthyl optionally substituted with one or two substituents selected from V and W as defined below;
$R^4$ is H or C$_1$-C$_4$-alkyl;
E is a single bond;
$R^6$ is C$_1$-C$_5$-alkyl;
A—B—C together are:
 (a) —C(R$^{7a}$)=C(R$^{7b}$)—Y—,
 (b) —Y—C(R$^{7a}$)=C(R$^{7b}$)—;
Y is S; R$^{7a}$ and R$^{7b}$ are independently:
 (a) H;

(b) straight chain or branched $C_1$-$C_6$-alkyl, which is optionally substituted with OH, $CO_2R^4$, $N(R^4)_2$ or $CON(R^4)_2$;

(c) aryl or aryl-$C_1$-$C_4$-alkyl wherein the aryl can be optionally substituted with H, halo, $C_1$-$C_4$-alkyl, hydroxy-$C_1$-$C_4$-alkyl, $C_1$-$C_4$-alkoxy or $CO_2R^4$;

(d) $CO_2R^4$;

(e) $CON(R^4)_2$;

(f) halo (Cl, Br, F, I);

$R^{21}$ is (a) aryl as defined above, (b) heteroaryl as defined above, (c) $C_3$-$C_7$-cycloalkyl;

X is:

(a) a single bond, (b) —CO—, (c) —O—, (d) —S—, (e) 

(f) 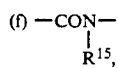

(g) 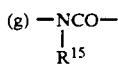

(h) —OCH$_2$, (i) —CH$_2$O—, (j) —SCH$_2$—, (k) —CH$_2$S—, (l) —NHC($R^9$)($R^{10}$)—, (m) $NR^9SO_2$—, (n) —$SO_2NR^9$—, (o) —C($R^9$)($R^{10}$)NH—, (p) —CH=CH—, (q) —CF=CF—, (r) —CH=CF—, (s) —CF=CH—, (t) —CH$_2$CH$_2$—, (u) —CF$_2$CF$_2$—, (v) 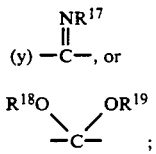

(w) 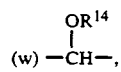

(x) 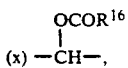

(y) $-\overset{\overset{NR^{17}}{\|}}{C}-$, or (z) $R^{18}O\diagdown\underset{-C-}{}\diagup OR^{19}$ ;

Z is $NR^{13}$; and r is 1 or 2.

2. The compound of claim 1 which is a member of the group:

(1) 6-methyl-2-propyl-3-[(2'-{1H-tetrazol-5-yl}-{1,1'-biphenyl}-4-yl)methyl]-3H-thieno[2,3-d]imidazole-5-methanol;

(2) 2-butyl-6-methyl-3-[(2'-{1H-tetrazol-5-yl}{1,1'-biphenyl}-4-yl)methyl]-3H-thieno[2,3-d]imidazole-5-carboxylic acid;

(3) 2-butyl-1-[(2'-{1H-tetrazol-5-yl}{1,1'-biphenyl}-4-yl)methyl]-1H-thieno[2,3-d]imidazole-5-carboxylic acid methyl ester;

(4) 2-butyl-3-[(2'-carboxy{1,1'-biphenyl}-4-yl)-methyl]-3H-thieno[2,3-d]imidazole-5-carboxylic acid methyl ester;

(5) 2-butyl-3-[(2'-{1H-tetrazol-5-yl}{1,1'-biphenyl}-4-yl)methyl]-3H-thieno[2,3-d]imidazole-5-carboxylic acid methyl ester;

(6) 2-butyl-1-[(2'-{1H-tetrazol-5-yl}{1,1'-biphenyl}-4-yl)methyl]-1H-thieno[2,3-d]imidazole-5-carboxylic acid methyl ester; and, (7) 2-butyl-1-[(2'-{(N-phenlsulfonyl)carboxamido}{1,1'-biphen}-4-yl)methyl]-1H-thieno[2,3-d]-imidazole-5-carboxylic acid methyl ester.

3. A pharmaceutical composition useful in the treatment of hypertension which comprises a pharmaceutically acceptable carrier and a pharmaceutically effective amount of a compound of claim 1.

4. A method of treating hypertension which comprises administering to a patient in need of such treatment a pharmaceutically effective amount of a compound of claim 1.

* * * * *